United States Patent
Lafaye et al.

(10) Patent No.: US 11,124,563 B2
(45) Date of Patent: *Sep. 21, 2021

(54) CAMELID SINGLE-DOMAIN ANTIBODY DIRECTED AGAINST PHOSPHORYLATED TAU PROTEINS AND METHODS FOR PRODUCING CONJUGATES THEREOF

(71) Applicants: F. HOFFMANN-LA ROCHE AG, Basel (CH); INSTITUT PASTEUR, Paris (FR); COMMISSARIAT A L'ENERGIE ATOMIQUE ET AUX ENERGIES ALTERNATIVES, Paris (FR); CENTRE NATIONAL DE LA RECHERCHE SCIENTIFIQUE (CNRS), Paris (FR)

(72) Inventors: Pierre Lafaye, Malakoff (FR); Sylvie Bay, Paris (FR); Benoit Delatour, Cachan (FR); Marc Dhenain, Limours (FR); Charles Duyckaerts, Saint-mandé (FR); Tengfei Li, Courbevoie (FR); Matthias Vandesquille, Fontenay-aux-roses (FR); Christian Czech, Grenzach-wyhlen (DE); Fiona Grueninger, Arlesheim (CH)

(73) Assignees: F. HOFFMANN-LA ROCHE AG, Basel (CH); INSTITUT PASTEUR, Paris (FR); COMMISSARIAT A L'ENERGIE ATOMIQUE ET AUX ENERGIES ALTERNATIVES, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 2 days.

This patent is subject to a terminal disclaimer.

(21) Appl. No.: 16/700,788

(22) Filed: Dec. 2, 2019

(65) Prior Publication Data

US 2020/0165329 A1 May 28, 2020

Related U.S. Application Data

(63) Continuation of application No. 16/141,914, filed on Sep. 25, 2018, now Pat. No. 10,538,582, which is a continuation of application No. 15/114,324, filed as application No. PCT/IB2015/050650 on Jan. 28, 2015, now Pat. No. 10,087,245.

(30) Foreign Application Priority Data

Jan. 28, 2014 (EP) .................................. 14152928

(51) Int. Cl.
*C07K 16/18* (2006.01)
*A61K 49/16* (2006.01)
*A61K 51/10* (2006.01)
*A61K 49/00* (2006.01)
*G01N 33/68* (2006.01)

(52) U.S. Cl.
CPC .......... *C07K 16/18* (2013.01); *A61K 49/0041* (2013.01); *A61K 49/0058* (2013.01); *A61K 49/16* (2013.01); *A61K 51/10* (2013.01); *G01N 33/6896* (2013.01); *C07K 2317/22* (2013.01); *C07K 2317/34* (2013.01); *C07K 2317/569* (2013.01); *G01N 2333/47* (2013.01); *G01N 2440/14* (2013.01); *G01N 2800/2821* (2013.01)

(58) Field of Classification Search
CPC ........................... C07K 16/18; C07K 2317/22; C07K 2317/34; C07K 2317/569; A61K 49/0041; A61K 49/0058; A61K 49/16; A61K 51/10; G01N 33/6896; G01N 2333/47; G01N 2440/14; G01N 2800/2821
See application file for complete search history.

(56) References Cited

U.S. PATENT DOCUMENTS

2011/0262427 A1* 10/2011 Hermans ............ C07K 16/2803
424/130.1

FOREIGN PATENT DOCUMENTS

| EP | 1876185 A1 | 1/2008 |
| WO | 2006/040153 A2 | 4/2006 |
| WO | WO-2010037818 A1 * | 4/2010 ........... C07K 16/244 |
| WO | 2010/142423 A2 | 12/2010 |

OTHER PUBLICATIONS

Li T et al. Camelid single-domain antibodies: A versatile tool for in vivo imaging of extracellular and intracellular brain targets. J. Controlled Release, 2016, 243, 1-10. (Year: 2016).*
Hasegawam et al: "Characterization of MABAP422, a Novel Phosphorylation-Dependentmonoclonal Antibody Against Tau Protein", FEBS Letters, Elsevier, Amsterdam, NL , vol. 384, Jan. 1, 1996 (Jan. 1, 1996), pp. 25-30.

(Continued)

*Primary Examiner* — Kimberly Ballard
(74) *Attorney, Agent, or Firm* — Arrigo, Lee, Guttman & Mouta-Bellum LLP

(57) ABSTRACT

The present invention relates to variable domains of a camelid heavy-chain antibodies directed against a phosphorylated tau protein and conjugates thereof. The present invention also relates to the use of these domains or conjugates for treating or diagnosing disorders mediated by neurofibrillary tangles, neuropil threads or dystrophic neurites, such as tauopathies.

20 Claims, 13 Drawing Sheets

Specification includes a Sequence Listing.

(56) References Cited

OTHER PUBLICATIONS

Bussiere T et al: "Phosphorylated serine422 on tau proteins is a pathological epitope found in several diseases with neurofibrillary degeneration", Actaneuropathologica, Springer Verlag, Berlin, DE, vol. 97, No. 3, Mar. 1, 1999 (Mar. 1, 1999), pp. 221-230.
Davies J et al: "Single Antibodydomains Assmallrecognitionunits:Designand in Vitro Antigen Selection of Camelized, Humanvh Domains With Improved Protein Stability", Protein Engineering, Oxford University Press,Surrey, GB, vol. 9 , No. 6 , Jan. 1, 1996 (Jan. 1, 1996) , pp. 531-537.
Davies J et al: "Camelising1 human antibody fragments: NMR studies on VH domains", FEBS Letters, Elsevier, Amsterdam, N L , vol. 339, No. 3, Feb. 21, 1994 (Feb. 21, 1994), pp. 285-290.

* cited by examiner

AD/VHH Tau-A2

AD/mAb AT8

FTD / VHH Tau-A2

PSP / VHH Tau-A2

VHH Tau-A2 mAb AT8

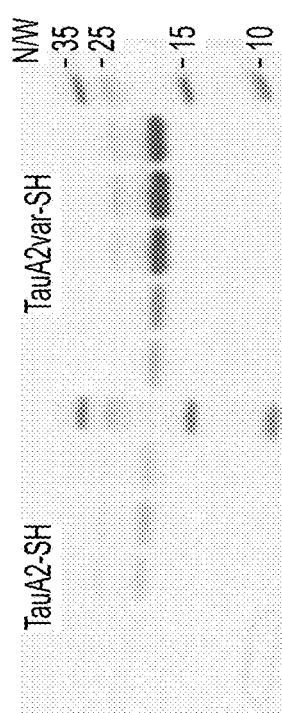
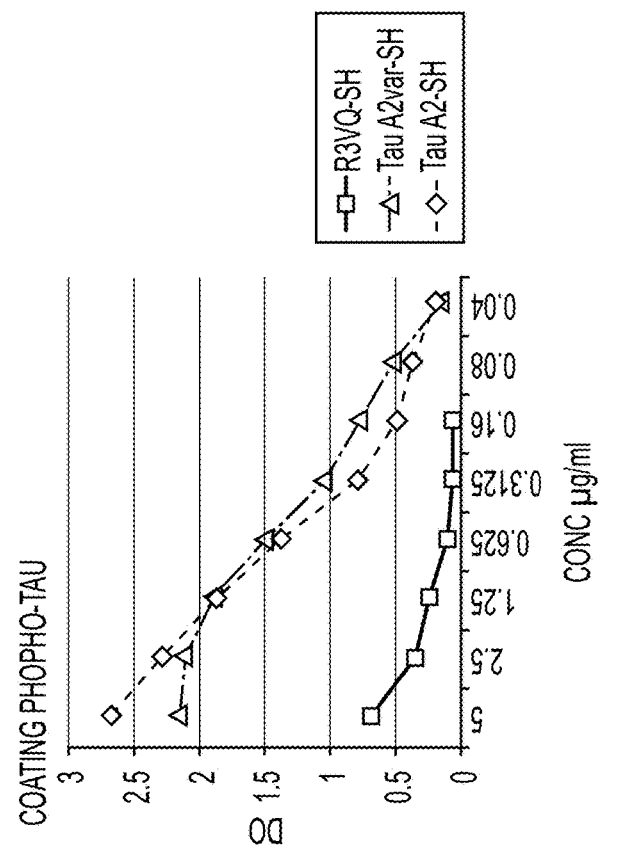
FIG. 11A
FIG. 11B
FIG. 11C

```
                         SEQUENCE LISTING

<160> NUMBER OF SEQ ID NOS: 17

<210> SEQ ID NO 1
<211> LENGTH: 13
<212> TYPE: PRT
<213> ORGANISM: Artificial Sequence
<220> FEATURE:
<223> OTHER INFORMATION: CDR1 of VHH Tau-A2

<400> SEQUENCE: 1

Ala Ala Ser Gly Arg Ser Phe Ser Gly Ser Thr Met Glu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: CDR2 of VHH Tau-A2

<400> SEQUENCE: 2

Ala Ile Arg Thr Ile Ser Ser Arg Thr Tyr Tyr Val Asp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: CDR3 of VHH Tau-A2

<400> SEQUENCE: 3

Arg Phe Ser Gly Thr Ile Gly Thr Thr Ser Ser Val Asp Tyr
1               5                   10

<210> SEQ ID NO 4
<211> LENGTH: 128
<212> TYPE: PRT
<213> ORGANISM: Lama pacos
<220> FEATURE:
<221> NAME/KEY: DOMAIN
<222> LOCATION: (25)..(37)
<223> OTHER INFORMATION: CDR1 of VHH Tau-A2
<220> FEATURE:
<221> NAME/KEY: DOMAIN
<222> LOCATION: (52)..(64)
<223> OTHER INFORMATION: CDR2 of VHH Tau-A2
<220> FEATURE:
<221> NAME/KEY: DOMAIN
<222> LOCATION: (101)..(114)
<223> OTHER INFORMATION: CDR3 of VHH Tau-A2

<400> SEQUENCE: 4

Met Ala Glu Val Gln Leu Gln Ala Ser Gly Gly Gly Leu Val Gln Ala
1               5                   10                  15

Gly Gly Ser Leu Arg Leu Ser Cys Ala Ala Ser Gly Arg Ser Phe Ser
            20                  25                  30

Gly Ser Thr Met Glu Trp Tyr Arg Gln Ala Pro Gly Lys Glu Arg Lys
        35                  40                  45
```

```
Phe Val Ala Ala Ile Arg Thr Ile Ser Ser Arg Thr Tyr Tyr Val Asp
 50                  55                  60

Ser Val Lys Gly Arg Phe Thr Ile Ser Arg Asp Ser Thr Lys Asn Thr
 65                  70                  75                  80

Val Tyr Leu Gln Leu Asn Ser Leu Lys Val Glu Asp Thr Ala Val Tyr
                 85                  90                  95

Tyr Cys Ala Ala Arg Phe Ser Gly Thr Ile Gly Thr Thr Ser Ser Val
                100                 105                 110

Asp Tyr Trp Gly Gln Gly Thr Gln Val Thr Val Ser Ser Ala Ala Ala
            115                 120                 125

<210> SEQ ID NO 5
<211> LENGTH: 119
<212> TYPE: PRT
<213> ORGANISM: Lama pacos

<400> SEQUENCE: 5

Gln Leu Gln Ala Ser Gly Gly Gly Leu Val Gln Ala Gly Gly Ser Leu
 1               5                  10                  15

Arg Leu Ser Cys Ala Ala Ser Gly Arg Ser Phe Ser Gly Ser Thr Met
                20                  25                  30

Glu Trp Tyr Arg Gln Ala Pro Gly Lys Glu Arg Lys Phe Val Ala Ala
            35                  40                  45

Ile Arg Thr Ile Ser Ser Arg Thr Tyr Tyr Val Asp Ser Val Lys Gly
 50                  55                  60

Arg Phe Thr Ile Ser Arg Asp Ser Thr Lys Asn Thr Val Tyr Leu Gln
 65                  70                  75                  80

Leu Asn Ser Leu Lys Val Glu Asp Thr Ala Val Tyr Tyr Cys Ala Ala
                85                  90                  95

Arg Phe Ser Gly Thr Ile Gly Thr Thr Ser Ser Val Asp Tyr Trp Gly
            100                 105                 110

Gln Gly Thr Gln Val Thr Val
            115

<210> SEQ ID NO 6
<211> LENGTH: 16
<212> TYPE: PRT
<213> ORGANISM: Artificial Sequence
<220> FEATURE:
<223> OTHER INFORMATION: single phospho-peptide derived from the
      C-terminus of the tau protein
<220> FEATURE:
<221> NAME/KEY: MISC_FEATURE
<222> LOCATION: (8)..(8)
<223> OTHER INFORMATION: Phosphorylation of the serine

<400> SEQUENCE: 6

Cys Ser Ile Asp Met Val Asp Ser Pro Gln Leu Ala Thr Leu Ala Asp
 1               5                  10                  15

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
cgccatcaag gtaccagttg a                                           21

<210> SEQ ID NO 8
```

```
<211> LENGTH: 29
<212> TYPE: DNA
<213> ORGANISM: Artificial Sequence
<220> FEATURE:
<223> OTHER INFORMATION: Primer

<400> SEQUENCE: 8
gatgtgcagc tgcaggcgtc tggrggagg                                    29

<210> SEQ ID NO 9
<211> LENGTH: 45
<212> TYPE: DNA
<213> ORGANISM: Artificial Sequence
<220> FEATURE:
<223> OTHER INFORMATION: Primer

<400> SEQUENCE: 9
catgccatga ctcgcggccc agccggccat ggccgakgts cagct                  45

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
ggactagttg cggccgctga ggagacggtg acctg                             35

<210> SEQ ID NO 11
<211> LENGTH: 4
<212> TYPE: PRT
<213> ORGANISM: Artificial Sequence
<220> FEATURE:
<223> OTHER INFORMATION: Spacer

<400> SEQUENCE: 11

Gly Gly Gly Ser
1

<210> SEQ ID NO 12
<211> LENGTH: 6
<212> TYPE: PRT
<213> ORGANISM: Artificial Sequence
<220> FEATURE:
<223> OTHER INFORMATION: His tag

<400> SEQUENCE: 12

His His His His His His
1               5

<210> SEQ ID NO 13
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 13

Leu Val Pro Arg Gly Ser
1               5

<210> SEQ ID NO 14
<211> LENGTH: 148
<212> TYPE: PRT
<213> ORGANISM: Artificial Sequence
<220> FEATURE:
```

```
<223> OTHER INFORMATION: VHH Tau-A2-SH
<220> FEATURE:
<221> NAME/KEY: DOMAIN
<222> LOCATION: (5)..(10)
<223> OTHER INFORMATION: 6xHis tag
<220> FEATURE:
<221> NAME/KEY: DOMAIN
<222> LOCATION: (14)..(19)
<223> OTHER INFORMATION: Thrombin cleavage site
<220> FEATURE:
<221> NAME/KEY: DOMAIN
<222> LOCATION: (23)..(141)
<223> OTHER INFORMATION: VHH Tau-A2
<220> FEATURE:
<221> NAME/KEY: DOMAIN
<222> LOCATION: (142)..(145)
<223> OTHER INFORMATION: Spacer
<220> FEATURE:
<221> NAME/KEY: DOMAIN
<222> LOCATION: (146)..(148)
<223> OTHER INFORMATION: Spacer

<400> SEQUENCE: 14

Met Gly Ser Ser His His His His His His Ser Ser Gly Leu Val Pro
1               5                   10                  15

Arg Gly Ser Ala Ala Ala Gln Leu Gln Ala Ser Gly Gly Gly Leu Val
            20                  25                  30

Gln Ala Gly Gly Ser Leu Arg Leu Ser Cys Ala Ala Ser Gly Arg Ser
        35                  40                  45

Phe Ser Gly Ser Thr Met Glu Trp Tyr Arg Gln Ala Pro Gly Lys Glu
    50                  55                  60

Arg Lys Phe Val Ala Ala Ile Arg Thr Ile Ser Ser Arg Thr Tyr Tyr
65                  70                  75                  80

Val Asp Ser Val Lys Gly Arg Phe Thr Ile Ser Arg Asp Ser Thr Lys
                85                  90                  95

Asn Thr Val Tyr Leu Gln Leu Asn Ser Leu Lys Val Glu Asp Thr Ala
            100                 105                 110

Val Tyr Tyr Cys Ala Ala Arg Phe Ser Gly Thr Ile Gly Thr Thr Ser
        115                 120                 125

Ser Val Asp Tyr Trp Gly Gln Gly Thr Gln Val Thr Val Gly Gly Gly
    130                 135                 140

Ser Cys Ser Ala
145

<210> SEQ ID NO 15
<211> LENGTH: 121
<212> TYPE: PRT
<213> ORGANISM: Artificial Sequence
<220> FEATURE:
<223> OTHER INFORMATION: VHH Tau-A2 variant

<400> SEQUENCE: 15

Asp Val Gln Leu Glu Ala Ser Gly Gly Gly Leu Val Gln Ala Gly Gly
1               5                   10                  15

Ser Leu Arg Leu Ser Cys Ala Ala Ser Gly Arg Ser Phe Ser Gly Ser
            20                  25                  30

Thr Met Glu Trp Tyr Arg Gln Ala Pro Gly Lys Glu Arg Lys Phe Val
        35                  40                  45

Ala Ala Ile Arg Thr Gly Ser Ser Arg Thr Tyr Tyr Val Asp Ser Val
    50                  55                  60

Lys Gly Arg Phe Thr Ile Ser Arg Asp Ser Thr Lys Asn Thr Val Tyr
65                  70                  75                  80
```

```
Leu Gln Leu Asn Ser Leu Lys Gly Glu Asp Thr Ala Val Tyr Tyr Cys
                85                  90                  95

Ala Ala Arg Phe Ser Gly Thr Ile Gly Thr Thr Ser Val Asp Tyr
            100                 105                 110

Trp Gly Gln Gly Thr Gln Val Thr Val
            115                 120

<210> SEQ ID NO 16
<211> LENGTH: 119
<212> TYPE: PRT
<213> ORGANISM: Artificial Sequence
<220> FEATURE:
<223> OTHER INFORMATION: VHH Tau-A2 variant

<400> SEQUENCE: 16

Gln Leu Glu Ala Ser Gly Gly Gly Leu Val Gln Ala Gly Gly Ser Leu
1               5                   10                  15

Arg Leu Ser Cys Ala Ala Ser Gly Arg Ser Phe Ser Gly Ser Thr Met
            20                  25                  30

Glu Trp Tyr Arg Gln Ala Pro Gly Lys Glu Arg Lys Phe Val Ala Ala
        35                  40                  45

Ile Arg Thr Gly Ser Ser Arg Thr Tyr Tyr Val Asp Ser Val Lys Gly
50                  55                  60

Arg Phe Thr Ile Ser Arg Asp Ser Thr Lys Asn Thr Val Tyr Leu Gln
65                  70                  75                  80

Leu Asn Ser Leu Lys Gly Glu Asp Thr Ala Val Tyr Tyr Cys Ala Ala
                85                  90                  95

Arg Phe Ser Gly Thr Ile Gly Thr Thr Ser Val Asp Tyr Trp Gly
            100                 105                 110

Gln Gly Thr Gln Val Thr Val
        115

<210> SEQ ID NO 17
<211> LENGTH: 150
<212> TYPE: PRT
<213> ORGANISM: Artificial Sequence
<220> FEATURE:
<223> OTHER INFORMATION: TauA2var-SH

<400> SEQUENCE: 17

Met Gly Ser Ser His His His His His His Ser Ser Gly Leu Val Pro
1               5                   10                  15

Arg Gly Ser Ala Ala Ala Asp Val Gln Leu Glu Ala Ser Gly Gly Gly
            20                  25                  30

Leu Val Gln Ala Gly Gly Ser Leu Arg Leu Ser Cys Ala Ala Ser Gly
        35                  40                  45

Arg Ser Phe Ser Gly Ser Thr Met Glu Trp Tyr Arg Gln Ala Pro Gly
    50                  55                  60

Lys Glu Arg Lys Phe Val Ala Ala Ile Arg Thr Gly Ser Ser Arg Thr
65                  70                  75                  80

Tyr Tyr Val Asp Ser Val Lys Gly Arg Phe Thr Ile Ser Arg Asp Ser
                85                  90                  95

Thr Lys Asn Thr Val Tyr Leu Gln Leu Asn Ser Leu Lys Gly Glu Asp
            100                 105                 110

Thr Ala Val Tyr Tyr Cys Ala Ala Arg Phe Ser Gly Thr Ile Gly Thr
        115                 120                 125
```

```
Thr Ser Ser Val Asp Tyr Trp Gly Gln Gly Thr Gln Val Thr Val Gly
    130                 135                 140

Gly Gly Ser Cys Ser Ala
145                 150
```

CAMELID SINGLE-DOMAIN ANTIBODY DIRECTED AGAINST PHOSPHORYLATED TAU PROTEINS AND METHODS FOR PRODUCING CONJUGATES THEREOF

The present invention relates to antibodies directed to phosphorylated tau proteins and conjugates thereof. The present invention also relates to the use of these antibody conjugates for treating or diagnosing disorders mediated by phosphorylated tau proteins.

About 70% of all cases of dementia are due to Alzheimer's disease (AD) which is associated with selective damage of brain regions and neural circuits critical for cognition. Alzheimer's disease is characterized by neurofibrillary tangles (NFTs) in particular in pyramidal neurons of the hippocampus and numerous amyloid plaques.

Ultrastructural studies on AD brain specimens have revealed that NFTs are primarily composed of paired helical filaments (PHFs), and these filaments are pairs of axially opposed fibrils of approximately 10 nm in diameter with a helical tridimensional conformation at a regular periodicity of 65 nm (Kidd 1963 *Nature*, 197, 192-3; Wiśniewski et al. 1976 *J Neurol Sci.*, 27, 173-81). In 1985, Brion et al. (*Archives de biologie (Bruxelles)*, 95, 229-235) demonstrated that the major component of the PHFs is the protein tau, a microtubulin associated protein (MAP). This result was confirmed by several authors: Grundke-Iqbal et al. 1986 *Proc Natl Acad Sci U.S.A.*, 83, 4913-7; Kosik et al. 1986 *Proc Natl Acad Sci U.S.A.*, 83, 4044-8; Delacourte and Defossez 1986 *J Neurol Sci.*, 76, 173-86; Wood et al. 1986 *Proc Natl Acad Sci U.S.A.*, 83, 4040-3; Nukina and Ihara 1986 *J Biochem.*, 99, 1541-4; Pollock et al. 1986 *Lancet*, 2, 1211; Montejo de Garcini et al. 1986 *Biochem Biophys Res Commun.*, 141, 790-6. It was then shown that the protein tau in NFTs was abnormally phosphorylated (Grundke-Iqbal and Iqbal, et al. 1986 *Proc Natl Acad Sci U.S.A.*, 83, 4913-7; Ihara et al. 1986 *J Biochem.*, 99, 1807-10; Iqbal et al. 1986 *Lancet*, 2, 421-6; Brion et al. 1986 *Lancet*, 2, 1098; Köpke et al. 1993 *J Biol Chem.*, 268, 24374-84), that leads to sequestration of normal tau and other MAPs (Alonso et al. 1994 *Proc Natl Acad Sci U.S.A.*, 91, 562-6; Alonso et al. 1997 *Proc Natl Acad Sci U.S.A.*, 94, 298-303), which causes disassembly of microtubules and thus impaired axonal transport, normal neuronal and synaptic functions, leading to loss of synapses and death of neurons. Hyperphosphorylated tau also becomes insoluble and self-aggregates into paired helical filaments (PHFs) and NFTs. The end of all these processes is dementia. Tau phosphorylation is regulated by the balance between multiple kinases and phosphatases (Iqbal et al. 2005 *Biochim Biophys Acta*, 1739, 198-210; Blennow et al. 2006 *Lancet*, 368, 387-403). With the increased amount of the abnormally phosphorylated tau, tau levels in the AD brain are around eightfold higher than in age-matched controls (Khatoon et al. 1992 *J Neurochem.*, 59, 750-3). Whether tau and NFT formation are a cause or consequence of AD is not currently known (Blennow et al. 2006 *Lancet*, 368, 387-403).

Tau was first isolated and identified as a MAP in the 70's (Weingarten et al. 1975 *Proc Natl Acad Sci U.S.A.*, 72, 1858-62; Cleveland et al. 1977 *J Mol Biol.*, 116, 227-47; Cleveland et al. 1977 *J Mol Biol.*, 116, 207-25) and is mainly expressed in neurons (Tucker 1990 *Brain Res Brain Res Rev.*, 15, 101-20; Schoenfeld and Obar 1994 *Int Rev Cytol.*, 151, 67-137). The human tau gene is located on chromosome 17 where it occupies over 100 kb and contains at least 16 exons (Neve et al. 1986 *Brain Res.*, 387, 271-80; Andreadis et al. 1992 *Biochemistry*, 31, 10626-33; Andreadis et al. 1995 *Nucleic Acids Res.*, 23, 3585-93). By alternative splicing, the tau gene yields different mRNA and results in the production of six tau isoforms (Goedert et al. 1989 *Neuron*, 3, 519-26; Himmler et al. 1989 *Mol Cel Biol.*, 9, 1381-8). The six tau isoforms differ from one another by the presence of three or four microtubule binding repeats (R) of 31-32 amino acids each and of one, two, or zero amino terminal inserts (N) of 29 amino acids each, giving rise to 0N3R, 1N3R, 2N3R, 0N4R, 1N4R, and 2N4R taus. The six isoforms of tau protein range from 352 to 441 amino acids (Goedert et al. 1989 *Neuron*, 3, 519-26; Himmler et al. 1989 *Mol Cell Biol.*, 9, 1381-8; Goedert et al. 1989 *The EMBO J.*, 8, 393-9). Each of these isoforms may exert specific physiological functions since they are differentially expressed during development. For example, 0N3R tau is the only isoform present in fetal brain while all six isoforms are expressed during adulthood (Kosik et al. 1989 *Neuron*, 2, 1389-97; Goedert and Jakes 1990 *EMBO J.*, 9, 4225-30; Buée et al. 2000 *Brain Res Brain Res Rev.*, 33, 95-130).

The 4R:3R tau ratios for both mRNA and protein are approximately equal in normal brain, but disturbances usually increase these ratios in most of the neurodegenerative tauopathies (Hanger et al. 2009 *Trends Mol Med.*, 15, 112-9). Using specific mAb, the hyperphosphorylated/pathological tau proteins can be visualized on Western blots as bands between 55 and 74 kDa (Buée et al. 2000 *Brain Res Brain Res Rev.*, 33, 95-130).

The tau441 (441 amino-acids) contains 80 serine/threonine and five tyrosine putative phosphorylation sites and an established function of tau is binding to microtubules through its microtubule-binding domains (R), thereby promoting microtubule assembly and stability (Weingarten et al. 1975 *Proc Natl Acad Sci U.S.A.*, 72, 1858-62; Cleveland et al. 1977 *J Mol Biol.*, 116, 227-47; Cleveland et al. 1977 *J Mol Biol.*, 116, 207-25; Bohm et al. 1990 *Acta Histochem Suppl.*, 39, 357-64; Nixon and Sihag 1991 *Trends Neurosci.*, 14, 501-6; Drechsel et al. 1992 *Mol Biol Cell.*, 3, 1141-54; Brandt and Lee 1993 *J Neurochem.*, 61, 997-1005). The microtubule assembly-promoting activity of tau is regulated by its degree of phosphorylation. Hyperphosphorylation suppresses the ability of tau to stimulate microtubule assembly (Lindwall and Cole 1984 *J Biol Chem.*, 259, 5301-5). AD hyperphosphorylation of tau at over 40 serine/threonine sites has been identified (Hasegawa et al. 1992 *J Biol Chem*, 267, 17047-54; Morishima-Kawashima et al. 1995 *J Biol Chem.*, 270, 823-9; Hanger et al. 1998 *Trends Mol Med*, 15, 112-9; Vega et al. 2005 *Brain Res Brain Mol Res.*, 138, 135-44). Phosphorylation of Ser202, the epitope recognized by AT8 mAb, was found to correlate with tangle formation and is reported to be an early marker of tau pathology of AD-type (Mercken et al. 1992 *Acta Neuropathol.*, 84, 265-72; Biernat et al. 1992 *EMBO J.*, 11, 1593-7; Su et al. 1994 *Neuroreport*, 5, 2358-62; Hernández et al. 2003 *Neurob Aging.*, 24, 1087-94; Blazquez-Llorca et al. 2011 *J Alzheimer's Dis.*, 26, 683-98). Phosphorylation of Ser422 near the C-terminus of tau is also reported to associate closely with development of NFTs. The amount of tau phosphorylated at Ser422 was found to increase with severity of AD and this phosphorylation site is also a prominent pathology in AD (Bussière et al. 1999 *Acta Neuropathol.*, 97, 221-30; Augustinack et al. 2002 *Acta Neuropathol.*, 103, 26-35; Haase et al. 2004 *J Neurochem.*, 88, 1509-20; Pennanen and Götz 2005 *Biochem Biophys Res Commun.*, 337, 1097-101; Deters et al. 2008 *Eur J Neurosci.*, 28, 137-47; Grueninger et al. 2011 *Mol Cell Biochem.*, 357, 199-207).

Unlike amyloid-beta (Aβ) deposits, NFTs develop in a stereotypical and predictable pattern in AD brain (Arnold et al. 1991 *Cereb Cortex*, 1, 103-16; Braak and Braak 1991 *Acta Neuropathol.*, 82, 239-59; Braak et al. 2006 *Acta Neuropathol.*, 112, 389-404). Braak and Braak (1991 *Acta Neuropathol.*, 82, 239-59) proposed six stages to describe progression of NFTs in their clinicopathological study. The first NFTs consistently appear in the transentorhinal (perirhinal) region (stage I) along with the entorhinal cortex proper, then spread in the CA1 region of the hippocampus (stage II). Next, NFTs develop and accumulate in limbic structures such as the subiculum of the hippocampal formation (stage III) and the amygdala, thalamus, and claustrum (stage IV). Finally, NFTs appear in all isocortical areas (isocortical stage), with the associative areas being affected prior and more severely (stage V), followed by the primary sensory, motor, and visual areas (stage VI). A severe involvement of striatum and substantia nigra can occur during the late isocortical stage (Serrano-Pozo, Frosch, et al. 2011 *Cold Spring Harb Perspect Med.*, 1, a006189). Multiple clinicopathological studies from different groups have established that NFT burden in the brain correlates with the severity and the duration of dementia (Arriagada et al. 1992 *Neurology*, 42, 631-9; Bierer et al. 1995 *Arch Neurol.*, 52, 81-8; Gómez-Isla et al. 1997 *Ann Neurol.*, 41, 17-2; Giannakopoulos et al. 2003 *Neurology*, 60, 1495-500; Ingelsson et al. 2004 *Neurology*, 62, 925-31). The selective distribution of NFTs described above matches with the hierarchical neuropsychological profile typical of the AD-type dementia syndrome (Serrano-Pozo et al. 2011 *Cold Spring Harb Perspect Med.*, 1, a006189).

In Alzheimer's disease (AD), accumulation of hyperphosphorylated and misfolded tau occurs in soma, dendrites and axons of neurons. Neurofibrillar tangles (NFTs) are related to the aggregated tau in the soma and are principally found in the medium-sized pyramidal neurons of the hippocampus, of the entorhinal cortex and of layers of the isocortex. Neuropil threads (Braak et al. 1986 *Neurosci Lett.*, 65, 351-5) are small, fragmented, tortuous processes, weaving between the cell bodies. These tortuous fibers (Duyckaerts et al. 1989 *Neuropathol Appl Neurobiol.*, 15, 233-47) contain PHFs that accumulate in dendrites of tangle-bearing neurons (Braak and Braak 1988 *Neuropathol Appl Neurobiol.*, 14, 39-44). Neuropil threads invariably accompany neurofibrillary tangles in AD and appear at an early stage of the neurofibrillary degeneration (Braak et al. 1994 *Acta Neuropathol.*, 87, 554-67). Finally, another tau lesion: dystrophic neurites containing hyperphosphorylated tau are found around neuritic plaques. They are mainly constituted of axonal processes enriched in paired helical filaments (PHF) (Kidd 1964 *Brain*, 87, 307-20). Interestingly, dystrophic neurites can also be immunoreactive for Amyloid Precursor Protein (APP), mitochondrial porin and chromogranin-A (Su et al. 1998 *Acta Neuropathol.*, 96, 463-71; Dickson et al. 1999 *Exp Neurol.*, 156, 100-10; Woodhouse et al. 2006 *Acta Neuropathol.*, 112, 429-37; Pérez-Gracia et al. 2008 *Acta Neuropathol.*, 116, 261-8).

Aside from Alzheimer's disease (AD), a family of related neurodegenerative diseases called tauopathies is also characterized by the deposition of tau-containing neurofibrillary tangles. These include progressive supranuclear palsy (PSP; Steele-Richardson-Olszewski disease), corticobasal degeneration (CBD), Pick's disease (PD), frontotemporal dementia with parkinsonism linked to chromosome 17 (FTDP-17) caused by tau mutations. In every one of these tauopathies the neurofibrillary pathology is made up of abnormally hyperphosphorylated tau and these pathological changes in the neocortex are associated with dementia. Different tau aggregates and filaments could be present in different diseases, raised by different composition of tau isoforms (tau 3R or 4R). For instance, in Pick's disease most of the tau is 3R isoform due to the exclusion of exon 10 which codes for the second microtubule binding repeat (R2). In contrast, in CBD and PSP, most of the tau is 4R (Morris et al. 1999 *Mov Dis.*, 14, 731-6; Sergeant et al. 2005 *Biochim Biophys Acta.*, 1739, 179-197; Yoshida 2006 *Neuropathology*, 26, 457-470; Liu and Gong 2008 *Mol Neurodegener.*, 3, 8; Zhong et al. 2012 *J Biol Chem.*, 287, 20711-9; Avila et al. 2013 *Aging Dis.*, 4, 23-8; Iqbal et al. 2013 *Front Neurol.*, 4, 112).

In vivo detection of amyloid plaques and tau lesions is critical to perform early diagnosis of Alzheimer's disease (AD) and of other tauopathies and to follow-up the effect of therapies. Current detection of these lesions is based on molecules that have a good affinity and specificity for these alterations. To date, in human, positron emission tomography (PET) and magnetic resonance imaging (MRI) have enabled visualization of amyloid plaques. However, the majority of compounds used in in vivo imaging modalities do not bind tau lesions. Therefore, there is a need to develop specific tau imaging agents. Recently, Maruyama et al. demonstrated the possibility to visualize in vivo tau lesions in AD patients using [$^{11}$C]-PBB3-PET (Maruyama et al. 2013 *Neuron.*, 79, 1094-108). Nevertheless, the need to radiolabel the compound and low spatial resolution are still the main disadvantages of PET-based methods. Conversely, MRI has a much higher spatial resolution and is widely available for animal and patient imaging. Even so, the low sensitivity of the MRI requires the development of dedicated contrast agents able to detect NFTs in patients.

Conventional immunoglobulins are heterotetramers composed of two heavy chains and two light chains with a combined molecular weight of about 150 kDa. In members of the family Camelidae a significant proportion of serum antibodies are homodimeric IgGs with a molecular weight of about 80 kD (Hamers-Casterman et al. 1993 *Nature*, 363, 446-448). These heavy chain immunoglobulins (Ig) contain three domains and their variable region is referred to as VHH. Recombinant VHHs (~12-14 kD in size) constitute intact antigen-binding domains and exhibit a broad antigen-binding repertoire. Their hypervariable regions are expanded and exhibit unique characteristics, such as the substitution of three to four hydrophobic framework residues (which interact with the $V_L$ in conventional antibodies) by more hydrophilic amino acids. To stabilize the enlarged CDRs, VHHs may possess in addition of the canonical disulfide bond, an extra disulfide bound between CDR1 and CDR3 in dromedaries and CDR2 and CDR3 in llamas (Harmsen and De Haard 2007 *Appl Microbiol Biotechnol.*, 77, 13-22; Muyldermans 2001 *J Biolechnol.*, 74, 277-302). The extended CDR3 loop can adopt a convex conformation, whereas conventional paratopes are limited to concave or flat structures (Muyldermans 2001 *J Biolechnol.*, 74, 277-302). These features allow VHHs to recognize unique epitopes that are poorly immunogenic for conventional antibodies (Lafaye et al. 2009 *Mol Immuno.*, 46, 695-704; Wernery 2001 *J Vet Med B Infect Dis Vet Public Health.*, 48, 561-568). Although VHHs are by definition monovalent antibodies, which by default exclude any avidity effect, their biological activity measured as $IC_{50}$ in vitro can be similar to conventional, bivalent antibody molecules (Thys et al. 2010 *Antiviral Res.*, 87, 257-264).

Methods, such as phage display, have been described to select antigen-specific VHH from VHH repertoires of immunized camels or llamas. The VHH genes are cloned in phage display vectors, the antigen binders are obtained by panning and selected VHH are expressed in bacteria. The recombinant VHHs have a number of advantages compared with the conventional antibody fragments (Fab or scFv), because only one domain has to be cloned and because these VHHs are well expressed, highly soluble in aqueous environments and are stable at high temperature. Because of their small size of about 12-14 kDa, VHHs rapidly pass the renal filter, which has a cutoff of about 60 kDa, resulting in rapid blood clearance. In addition, the small size results in a fast tissue penetration. The VHH short serum half-life of about 2 hours, compared to 4 h for scFv and 50 h for IgG, is advantageous for in vivo diagnosis using imaging and for the targeting of VHHs coupled to a substance of interest for treating a disorder, as one can expect that unspecifically bound VHH will be quickly removed from the tissues. Further, a VHH having an isoelectric point of at least 8.5 is able to transmigrate across the BBB by micropinocytosis and absorptive-mediated endocytosis. Such a VHH can be used for the preparation of a peptide vector for delivering a substance of interest across a mammal blood-brain barrier (International Applications WO 2009/004495 and WO 2010/004432).

Within the framework of research that has led to the present invention, the inventors have immunized two alpacas (*Lama pacos*) against a phosphorylated-tau (phospho-tau, phosphor-tau or p-tau) enriched Alzheimer's disease brain (hippocampal) extract and phospho-tau proteins. VHHs targeting phospho-tau were identified by phage display library construction and panning. Following bacterial expression, selected VHHs were screened by immunobloting and ELISA against p-tau epitopes before being tested on brain sections from human cases with neuropathologically-confirmed AD or other tauopathies and from transgenic mouse model harboring tangles pathologies. The inventors identified a VHH, referred to as Tau-A2 or A2, that immunolabels somatic tangles, neuropil threads and dystrophic neurites in mutated tau transgenic mice as well as in AD human brain samples. In addition VHH Tau-A2 allows detection of glial p-tau inclusions in other tauopathies, fronto-temporal dementia, corticobasal degeneration and progressive supranuclear palsy. This VHH Tau-A2 has the amino acid sequence SEQ ID NO. 4, that comprises a CDR1 (Complementarity Determining Region 1) of amino acid sequence SEQ ID NO. 1, a CDR2 of amino acid sequence SEQ ID NO. 2 and a CDR3 of amino acid sequence SEQ ID NO. 3. VHH Tau-A2 specifically recognizes the phosphorylated serine 422 (pS422) in a C-ter tau phospho-peptide. Further, labeling of VHH Tau-A2 with the paramagnetic agent gadolinium (Gd) or Alexa Fluor® 488 fluorophore was performed using a site-specific coupling approach, resulting in functionally effective VHH conjugates. After intravenous administration of fluorescent VHH Tau-A2, live two-photon microscopy showed gradual extravasation of the VHH Tau-A2 from blood vessels and penetration in brain parenchyma with an exquisite tropism for tangles.

Accordingly, the present invention provides an isolated variable domain of a camelid heavy-chain antibody (referred to as VHH), characterized in that it is directed against a phosphorylated tau protein, preferably directed against the phosphorylated serine 422 of a phosphorylated tau protein.

As used herein, a tau protein refers to the well known six isoforms of tau protein (Goedert et al. 1989 *Neuron*, 3, 519-26; Himmler et al. 1989 *Mol Cel Biol.*, 9, 1381-8), preferably the 4R isoform.

In a preferred embodiment, the VHH of the invention is obtainable by immunizing a camelid with the single phospho-peptide derived from the C-terminus of a tau protein of sequence CSIDMVDS(PO$_3$H$_2$)PQLATLAD (SEQ ID NO. 6) or a phospho-tau enriched Alzheimer's disease brain (preferably hippocampal) extract from a human or a phosphorylated tau protein such as a phosphorylated tau protein wherein the serine 422 thereof is phosphorylated, preferably with the single phospho-peptide derived from the C-terminus of a tau protein of sequence CSIDMVDS(PO$_3$H$_2$)PQLATLAD (SEQ ID NO. 6).

A phospho-tau enriched Alzheimer's disease brain (preferably hippocampal) extract from a human can be obtained as described in Mercken et al. 1992 *Acta Neuropathol.*, 84, 265-272.

Advantageously, the VHH of the invention is obtainable by the method comprising the steps of:

(a) immunizing a camelid, preferably a *Lama pacos*, with the single phospho-peptide derived from the C-terminus of a tau protein of sequence CSIDMVDS(PO$_3$H$_2$)PQLATLAD (SEQ ID NO. 6) or a phospho-tau enriched Alzheimer's disease brain (preferably hippocampal) extract from a human or a phosphorylated tau protein such as a phosphorylated tau protein wherein the serine 422 thereof is phosphorylated, preferably with the single phospho-peptide derived from the C-terminus of a tau protein of sequence CSIDMVDS(PO$_3$H$_2$)PQLATLAD (SEQ ID NO. 6), (b) isolating peripheral lymphocytes of the immunized camelid, obtaining the total RNA and synthesizing the corresponding cDNAs (methods are known in the art; for instance see Lafaye et al. 1995 *Res Immunol.*, 146, 373-82; Erratum in: 1996, *Res Immunol.*, 147, 61), (c) constructing a library of cDNA fragments encoding VHH domains, (d) transcribing the VHH domain-encoding cDNAs obtained in step (c) to mRNA using PCR, converting the mRNA to ribosome display format, and selecting the VHH domain by ribosome display, and (e) expressing the VHH domain in a vector, for instance, a suitable vector is pET22 (Novagen, Cat. No. 69744-3) and, optionally purifying the expressed VHH domain.

In a preferred embodiment of said method, in step (a), the camelid is immunized at days 0, 21 and 40 with 500 µg of the peptide of sequence CSIDMVDS(PO$_3$H$_2$)PQLATLAD (SEQ ID NO. 6) or a phospho-tau enriched Alzheimer's disease brain (preferably hippocampal) extract from a human or a phosphorylated tau protein wherein the serine 422 thereof is phosphorylated. The bound camelid antibodies can be detected with polyclonal rabbit anti-camelid IgG (for instance, see Muyldermans 1994 *Protein Eng.*, 7, 1129-35) and horseradish peroxidase-labeled goat anti-rabbit antibodies.

In another preferred embodiment of said method, in step (c), said library can be constructed by amplifying by PCR the DNA fragments encoding the VHH domains, and ligating the PCR products obtained into a phage vector (an example of suitable phage vector is pHEN; Hoogenboom et al. 1992 *J Mol Biol.*, 227, 381-8).

In a particular embodiment of said step (c), the DNA fragments encoding VHH domains are amplified by PCR using the primers of sequences SEQ ID NO. 7 (named CH2FORTA4) and SEQ ID NO. 8 (named VHBACKA6), and the amplified product is subjected to a second round of PCR using either of the primers of sequences SEQ ID NO. 9 (named VHBACKA4) and SEQ ID NO. 10 (named VHFOR36). Such a method is described in the International PCT Application No. WO 2004/044204.

Ribosome display technology enables in vitro selection of a protein together with the mRNA that encodes it. A DNA library coding for particular proteins, for instance VHH fragments, is transcribed in vitro. The mRNA is purified and used for in vitro translation. As the mRNA lacks a stop codon, the ribosome stalls at the end of the mRNA, giving rise to a ternary complex of mRNA, ribosome and functional protein (Hanes and Plückthun 1997 *Proc Natl Acad Sci U.S.A.*, 94, 4937-42). A library of these ternary complexes is tested against the potential ligand (in the case of antibodies, against the antigen). The binding of the ternary complex (ribosome, mRNA, protein) to the ligand allows the recovery of the encoding mRNA that is linked to it and that can be transcribed into cDNA by Reverse Transcriptase-PCR (RT-PCR). Cycles of selection and recovery can be iterated both to enrich rare ligand-binding molecules, and to select molecules with the best affinity. Methods for ribosome display selections are known in the art; see for instance Mouratou et al. 2007 *Proc Natl Acad Sci U.S.A.*, 104, 17983-8.

In a preferred embodiment of the VHH of the invention, its amino acid sequence comprises, from the N-terminus to the C-terminus, the amino acid sequence SEQ ID NO. 1 (corresponding to the CDR1 of the VHH), the amino acid sequence SEQ ID NO. 2 (corresponding to the CDR2) and the amino acid sequence SEQ ID NO. 3 (corresponding to the CDR3).

In a more preferred embodiment, said VHH consists of the amino acid sequence:
  SEQ ID NO. 4, corresponding to the full-length form of VHH Tau-A2 or
  SEQ ID NO. 5, corresponding to a short form of VHH Tau-A2.

As used herein, the term "isolated" refers to a VHH which has been separated from a component of its natural environment. In some embodiments, a VHH is purified to greater than 95% or 99% purity as determined by, for example, electrophoretic (e.g., SDS-PAGE, isoelectric focusing (IEF), capillary electrophoresis) or chromatographic (e.g., gel filtration, ion exchange or reverse phase HPLC). For review of methods for assessment of antibody purity, see, e.g., Flatman et al. 2007 *J Chromatogr B Analyt Technol Biomed Life Sci.*, 848, 79-87.

As used herein, the term "VHH" refers to the variable antigen-binding domain from a camelid (camel, dromedary, llama, alpaca, etc.) heavy-chain antibody (See Nguyen et al. 2000 *EMBO J.*, 19, 921-930; Muyldermans 2001 *J Biotechnol.*, 74, 277-302 and for review Vanlandschoot et al. 2011 *Antiviral Res.* 92, 389-407). A VHH can also be named Nanobody (Nb).

Advantageously, the VHH according to the present invention has a basic isoelectric point (pI), preferably between 8.5 and 10.5, and more preferably between 9.5 and 10.5.

The invention encompasses natural, recombinant or synthetic VHHs as defined above.

As used herein, the term "recombinant" refers to the use of genetic engineering methods (cloning, amplification) to produce said VHH.

As used herein, the term "synthetic" refers to the production of said VHH by in vitro chemical and/or enzymatic synthesis.

The VHH according to the present invention can be in the form of a monomer or a homomultimer, such as a homodimer or a homotrimer.

The present invention also provides a method for obtaining a VHH directed against a phosphorylated tau protein as defined above comprising a step of immunizing a camelid with the single phospho-peptide derived from the C-terminus of a tau protein of sequence CSIDMVDS(PO$_3$H$_2$)PQLATLAD (SEQ ID NO. 6) or a phospho-tau enriched Alzheimer's disease brain (preferably hippocampal) extract from a human or a phosphorylated tau protein such as a phosphorylated tau protein wherein the serine 422 thereof is phosphorylated, preferably comprising the steps (a) to (e) as defined above.

The present invention also provides an isolated camelid serum, preferably an alpaca serum, comprising a VHH according to the present invention.

The present invention also provides an isolated variant of the VHH Tau-A2 of SEQ ID NO. 5, wherein said VHH variant is directed against the phosphorylated serine 422 of a phosphorylated tau protein as defined above, and wherein the amino acid sequence of said variant has at least 95% identity, or by order of increasing preference at least 96%, 97%, 98% or 99% identity, with the amino acid sequence SEQ ID NO: 5.

Unless otherwise specified, the percents of identity between two sequences which are mentioned herein are calculated from an alignment of the two sequences over their whole length.

In a preferred embodiment of said variant, the amino acid sequence thereof comprises, from the N-terminus to the C-terminus, the amino acid sequence SEQ ID NO. 1, the amino acid sequence SEQ ID NO. 2 and the amino acid sequence SEQ ID NO. 3.

In another preferred embodiment, said variant has the amino acid sequence SEQ ID NO. 5 having the following mutations:
  the Glutamine residue (Gln, Q) at position 3 of the amino acid sequence SEQ ID NO. 5 is substituted with an amino acid residue selected from the group consisting of Aspartic acid (Asp, D) and Glutamic acid (Glu, E), preferably Glu,
  the Isoleucine residue (Ile, I) at position 52 of the amino acid sequence SEQ ID NO. 5 is substituted with an amino acid residue selected from the group consisting of Alanine (Ala, A) and Glycine (Gly, G), preferably Gly,
  the Valine residue (Val, V) at position 86 of the amino acid sequence SEQ ID NO. 5 is substituted with an amino acid residue selected from the group consisting of Alanine (Ala, A), Serine (Ser, S), Threonine (Thr, T), Asparagine (Asn, N), Glutamine (Gln, Q), Aspartic acid (Asp, D), Glutamic acid (Glu, E), Lysine (Lys, K), Arginine (Arg, R) and Glycine (Gly, G), preferably Gly,
  and optionally two amino acid residues are added in N-terminal position of the amino acid sequence SEQ ID NO. 5 and are selected from the group consisting of the dipeptides Glutamic acid-Valine (E-V) and Aspartic acid-Valine (D-V), preferably D-V.

In a particular embodiment, said VHH variant consists in the amino acid sequence SEQ ID NO: 15.

In another particular embodiment, said VHH variant consists in the amino acid sequence SEQ ID NO: 16 (this VHH variant does not comprise an added dipeptide in N-terminal position compared to the amino acid sequence SEQ ID NO. 5).

The present invention also provides a VHH derivative consisting of a polypeptide comprising a VHH or a VHH variant (preferably the VHH variant of SEQ ID NO. 15) according to the present invention, provided that said VHH or VHH variant comprised in said polypeptide is able to bind a phosphorylated tau protein, preferably the phosphorylated serine 422 of a phosphorylated tau protein.

In another particular embodiment, said VHH derivative has the formula P-C-Z or Z-C-P, preferably P-C-Z, wherein:
  P is a 100-500, preferably 100-150, amino acid peptide comprising or consisting of a VHH or VHH variant according to the present invention, wherein said amino acid sequence has no accessible reduced cystein residue, and preferably has no reduced cystein residue, C is a cystein residue, Z is a 1-10 amino acid spacer, preferably a 1-10 neutral or negatively charged amino acid spacer, wherein the amino acid residues of Z are identical or different and wherein Z does not contain a cystein residue.

In the sense of the invention, the expression "no accessible reduced cystein residue" refers to a cystein residue which is not accessible for a conjugation step as defined according to the invention.

In a preferred embodiment, the VHH derivative has the formula P-C-Z or Z-C-P, preferably P-C-Z, wherein:

P is a 100 to 500, preferably 100-150, amino acid peptide having no accessible reduced cystein residue, and preferably has no reduced cystein residue, C is a cystein residue, Z represents a) a 2-10 amino acid spacer, preferably a 2 amino acid spacer, wherein the amino acid residues of Z are selected from the group consisting of serine (S), alanine (A), valine (V) and glycine (G), and more preferably serine (S), alanine (A) and valine (V), and wherein at least two amino acid residues of Z are different, or b) a 2-10 amino acid spacer, preferably a 2-10 neutral or negatively charged amino acid spacer, wherein Z comprises the dipeptide serine-alanine (S-A) or serine-valine (S-V) and wherein Z does not contain a cystein residue.

Advantageously, the cystein residue C is sterically accessible.

Advantageously, the amino acid residues of the amino acid spacer Z are selected from the group consisting of alanine, valine, serine, leucine, isoleucine, phenylalanine, glycine, serine, threonine, tyrosine, asparagine and glutamine, preferably alanine, valine and serine.

Advantageously, when Z is as defined in a), the amino acid spacer Z comprises 1 or at least 1 serine, more advantageously, the amino acid spacer Z consists in serine and alanine residues only or in serine and valine residues only.

In a preferred embodiment of this VHH derivative, the amino acid spacer Z consists of a 2 amino acid sequence, such as the amino acid sequences S-A or S-V.

The amino acid sequence P of the VHH derivative of formula P-C-Z can have at its C-terminus a 1-10 amino acid spacer Y, preferably a 1-10 neutral or negatively charged amino acid spacer, wherein the amino acid residues of said amino acid spacer Y are identical or different, and wherein said amino acid spacer Y does not contain a cystein residue.

The amino acid sequence P of the VHH derivative of formula Z-C-P can have at its N-terminus a 1-10 amino acid spacer Y, preferably a 1-10 neutral or negatively charged amino acid spacer, wherein the amino acid residues of said amino acid spacer Y are identical or different, and wherein said amino acid spacer Y does not contain a cystein residue.

Advantageously, the amino acid residues of the amino acid spacer Y are selected from the group consisting of alanine, valine, serine, leucine, isoleucine, phenylalanine, glycine, serine, threonine, tyrosine, asparagine and glutamine, preferably alanine, valine, serine and glycine.

Preferably, the amino acid spacer Y represents a 4 neutral amino acid spacer, such as the amino acid sequence G-G-G-S (SEQ ID NO. 11).

The amino acid sequence P of the VHH derivative of formula P-C-Z can also have at its N-terminus a 1-50 amino acid sequence X, wherein the amino acid residues of said amino acid sequence X are identical or different, and wherein said amino acid sequence X does not contain a cystein residue.

The amino acid sequence P of the VHH derivative of formula Z-C-P can also have at its C-terminus a 1-50 amino acid sequence X, wherein the amino acid residues of said amino acid sequence X are identical or different, and wherein said amino acid sequence X does not contain a cystein residue.

The amino acid sequence X can comprise a tag such as a 6×His tag (SEQ ID NO. 12) and an enzyme cleavage site, such as the thrombin cleavage site of amino acid sequence LVPRGS (SEQ ID NO. 13).

In a preferred embodiment, the VHH derivative according to the present invention has the formula P'-C-Z, P'-Y-C-Z, X-P'-C-Z, X-P'-Y-C-Z, Z-C-P', Z-C-Y-P', Z-C-P'-X, or Z-C-Y-P'-X, wherein P' is a VHH or VHH variant according to the present invention.

The present invention also provides an isolated oligopeptide of formula P-C-Z or Z-C-P, preferably P-C-Z as defined above.

Advantageously, said VHH derivative comprises, from the N-terminus to the C-terminus, an amino acid tag such as a 6×His tag, an enzyme cleavage site, such as a thrombin cleavage site, a VHH or VHH variant according to the present invention, an amino acid spacer, a cystein and a second amino acid spacer. Such a VHH derivative corresponds to a VHH derivative of formula X-P'-Y-C-Z, wherein P' is a VHH or VHH variant.

In a preferred embodiment, said VHH derivative has the amino acid sequence SEQ ID NO. 14 (Tau-A2-SH).

In another preferred embodiment, said VHH derivative has the amino acid sequence SEQ ID NO. 17 (Tau-A2var-SH). This VHH derivative comprises the VHH variant of SEQ ID NO. 15 according to the invention.

The present invention also provides an isolated polynucleotide encoding a VHH, or VHH variant or a VHH derivative according to the present invention.

A polynucleotide according to the present invention may be obtained by well-known methods of recombinant DNA technology and/or of chemical DNA synthesis.

The present invention also provides a recombinant expression cassette comprising a polynucleotide according to the present invention under the control of a transcriptional promoter allowing the regulation of the transcription of said polynucleotide in a host cell. Said polynucleotide can also be linked to appropriate control sequences allowing the regulation of its translation in a host cell.

The present invention also provides a recombinant vector (e.g., a recombinant expression vector) comprising a polynucleotide according to the present invention. Advantageously, said recombinant vector is a recombinant expression vector comprising an expression cassette according to the present invention.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The present invention also provides a host cell containing a recombinant expression cassette or a recombinant vector according to the present invention. The host cell is either a prokaryotic or eukaryotic host cell.

The terms "host cell" refers to a cell into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A prokaryotic host cell expressing VHH Tau-A2 of amino acid sequence SEQ ID NO. 4 with a 6xHistidine tag was deposited on Jan. 16, 2014, at the Collection Nationale de Cultures de Microorganismes (CNCM), 28 rue du Dr Roux, 75724 Paris Cedex 15, France, under the number 1-4835.

A prokaryotic host cell expressing VHH Tau-A2-SH of amino acid sequence SEQ ID NO. 14 was deposited on Jan. 16, 2014, at the Collection Nationale de Cultures de Microorganismes (CNCM), 28 rue du Dr Roux, 75724 Paris Cedex 15, France, under the number 1-4836.

A prokaryotic host cell expressing VHH Tau-A2var-SH (also named TauA2 VAR-SH) of amino acid sequence SEQ ID NO. 17 was deposited on Jan. 21, 2015, at the Collection Nationale de Cultures de Microorganismes (CNCM), 28 rue du Dr Roux, 75724 Paris Cedex 15, France, under the number 1-4951.

The present invention also provides a method for producing in a host cell as defined above an oligopeptide of formula P-C-Z or Z-C-P according to the present invention, comprising the steps of:

providing a host cell containing a recombinant expression cassette or a recombinant vector according to the present invention, culturing said host cell, and optionally purifying the oligopeptide of formula P-C-Z or Z-C-P.

Methods for purifying an oligopeptide are well known in the art, such as chromatography (e.g., ion exchange chromatography, gel permeation chromatography and reversed phase chromatography).

The present invention also provides a diagnostic or therapeutic agent comprising a VHH, a VHH variant or a VHH derivative (in particular a VHH derivative of formula P-C-Z or Z-C-P as defined above) according to the present invention, linked, directly or indirectly, covalently or non-covalently to a substance of interest.

The substance of interest according to the present invention may or may not permeate the mammal or human blood-brain barrier. If the substance of interest permeates said blood-brain barrier, then the use of a VHH, a VHH variant or a VHH derivative (in particular a VHH derivative of formula P-C-Z or Z-C-P as defined above) according to the present invention can allow enhancing the delivery of said substance of interest across the blood-brain barrier.

In an embodiment, said substance of interest is a diagnostic or therapeutic compound.

In another embodiment, said substance of interest is a liposome or a polymeric entity comprising a diagnostic or therapeutic compound (Villaraza et al. 2010 *Chem Rev.*, 110, 2921-2959).

Advantageously, said diagnostic compound is selected from the group consisting of:

an enzyme such as horseradish peroxidase, alkaline phosphatase, glucose-6-phosphatase or beta-galactosidase;

a fluorophore such as green fluorescent protein (GFP), blue fluorescent dyes excited at wavelengths in the ultraviolet (UV) part of the spectrum (e.g. AMCA (7-amino-4-methylcoumarin-3-acetic acid); Alexa Fluor® 350), green fluorescent dyes excited by blue light (e.g. FITC, Cy2, Alexa Fluor® 488), red fluorescent dyes excited by green light (e.g. rhodamines, Texas Red, Cy3, Alexa Fluor dyes 546, 564 and 594), or dyes excited with far-red light (e.g. Cy5) to be visualized with electronic detectors (CCD cameras, photomultipliers);

a radioisotope such as $^{18}$F, $^{11}$C, $^{13}$N, $^{15}$O, $^{68}$Ga, $^{82}$Rb, $^{44}$Sc, $^{64}$Cu, $^{86}$Y, $^{89}$Zr, $^{124}$I, $^{152}$Tb that can be used for PET imaging or $^{67}$Ga, $^{81m}$Kr, $^{99m}$Tc, $^{111}$In, $^{123}$I, $^{125}$I, $^{133}$Xe, $^{201}$Tl, $^{155}$Tb, $^{195m}$Pt that can e used for SPECT/scintigraphic studies, or $^{14}$C, $^{3}$H, $^{35}$S, $^{32}$P, $^{125}$I that can be used for autoradiography or in situ hybridisation, or $^{211}$At-, $^{212}$Bi-, $^{75}$Br-, $^{76}$Br-, $^{131}$I-, $^{111}$In, $^{177}$Lu-, $^{212}$Pb-, $^{186}$Re-, $^{188}$Re-, $^{153}$Sm-, $^{90}$Y that can be used to label the compounds;

a NMR or MRI contrast agent such as the paramagnetic agents gadolinium (Gd), dysprosium (Dy) and manganese (Mn), and the superparamagnetic agents based on iron oxide (such as MION, SPIO or USPIO) or iron platinium (SIPP), and X-nuclei such as $^{18}$F, $^{13}$C, $^{23}$Na, $^{17}$O, $^{15}$N;

a nanoparticle such as gold nanoparticles (B. Van de Broek et al., ACSNano, Vol. 5, No. 6, 4319-4328, 2011) or quantum dots (A. Sukhanova et al., 2012 *Nanomedicine*, 8 516-525).

In a preferred embodiment, said diagnostic compound is a fluorophore, more preferably Alexa Fluor® 488, or a MRI contrast agent, more preferably gadolinium.

When the diagnostic agent is used for detection, it may comprise a radioactive atom for scintigraphic studies, for example $^{99}$Tc or $^{123}$I, or a spin label for nuclear magnetic resonance (NMR) imaging (also known as MRI), such as $^{13}$C, $^{9}$F, Fe, Gd, $^{123}$I, $^{111}$In, Mn, $^{15}$N or $^{7}$O.

Advantageously, said therapeutic compound is selected from a peptide, an enzyme, a nucleic acid, a virus and a chemical compound. It can be an analgesic compound, an anti-inflammatory compound, an antidepressant compound, an anticonvulsant compound, a cytotoxic compound or an anti-neurodegenerative compound.

The substance of interest as defined above can be directly and covalently or non-covalently linked to the VHH, VHH variant or VHH derivative (in particular a VHH derivative of formula P-C-Z or Z-C-P as defined above) according to the present invention either to one of the terminal ends (N or C terminus) of said VHH, VHH variant or VHH derivative (in particular a VHH derivative of formula P-C-Z or Z-C-P as defined above), or to the side chain of one of the amino acids of said VHH, VHH variant or VHH derivative. The substance of interest can also be indirectly and covalently or non-covalently linked to said VHH, VHH variant or VHH derivative by means of a spacer either to one of the terminal ends of said VHH, VHH variant or VHH derivative (in particular a VHH derivative of formula P-C-Z or Z-C-P as defined above), or to a side chain of one of the amino acids of said VHH, VHH variant or VHH derivative. Conventional linking methods of a substance of interest to a peptide, in particular an antibody, are known in the art (e.g., See Ternynck and Avrameas 1987 "Techniques immunoenzymatiques" Ed. INSERM, Paris; Hermanson, 2010, Bioconjugate Techniques, Academic Press).

Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

The VHH, VHH variant or VHH derivative (in particular a VHH derivative of formula P-C-Z or Z-C-P as defined above) according to the present invention may be labeled with specific radioisotopes or NMR or MRI contrast agents or fluorophores or nanoparticles or enzymes using general organic chemistry techniques known in the art. See, e.g., March, J. ADVANCED ORGANIC CHEMISTRY: REACTIONS, MECHANISMS, AND STRUCTURE (3rd Edition, 1985); Hermanson, 2010, Bioconjugate Techniques, Academic Press.

In addition, the VHH, VHH variant or VHH derivative according to the present invention also may be labeled with any suitable radioactive iodine isotope, such as, but not limited to $^{131}$I, $^{125}$I, or $^{123}$I, by iodination of a diazotized amino derivative directly via a diazonium iodide (see Greenbaum 1936 *F Am J Pharm.*, 108, 17), or by conversion of the unstable diazotized amine to the stable triazene, or by conversion of a non-radioactive halogenated precursor to a stable tri-alkyl tin derivative which then can be converted to the iodo compound by several methods well known to the art. See, Satyamurthy and Barrio 1983 *J Org Chem.*, 48, 4394; Goodman et al. 1984 *J Org Chem.*, 49, 2322; Mathis et al. 1994 *J Labell Comp Radiopharm.*, 905; Chumpradit et al. 1991 *J Med Chem.*, 34, 877; Zhuang et al. 1994 *J Med Chem.*, 37, 1406; Chumpradit et al. 1994 *J Med Chem.*, 37, 4245.

In particular, the VHH, VHH variant or VHH derivative according to the present invention can be labeled with $^{123}$I for SPECT by any of several techniques known to the art. See, e.g., Kulkarni 1991 *Int J Rad Appl Inst.* (Part B) 18, 647.

The VHH, VHH variant or VHH derivative according to the present invention also may be radiolabeled with known metal radiolabels, such as Technetium-99m ($^{99m}$Tc). Modification of the substituents to introduce ligands that bind such metal ions can be effected without undue experimentation by one of ordinary skill in the radiolabeling art. The metal radiolabeled VHH, VHH variant or VHH derivative according to the present invention can then be used to detect neurofibrillary tangles, neuropil threads or dystrophic neurites. Preparing radiolabeled derivatives of $^{99m}$Tc is well known in the art. See, for example, Zhuang et al. 1999 *Nucl Med Biol.*, 26, 217-24; Oya et al. 1998 *Nucl Med Biol.*, 25, 135-40; Horn et al. 1997 *Nucl Med Biol.*, 24, 485-98.

The invention also relates to coupling methods for obtaining a VHH, VHH variant or VHH derivative (in particular a VHH derivative of formula P-C-Z or Z-C-P as defined above) according to the invention coupled, directly or indirectly, with a substance of interest (functional conjugate).

According to a first strategy, a VHH, VHH variant or VHH derivative according to the invention is conjugated to a substance of interest by using a non-site specific approach. Said non-site specific method comprises a conjugation step of a substance of interest with a VHH, VHH variant or VHH derivative according to the invention.

When the substance of interest is a metal, such as a NMR or MRI contrast agent (for example, paramagnetic agents gadolinium (Gd), dysprosium (Dy) and manganese (Mn), and superparamagnetic agents based on iron oxide or iron platinum, and X-nuclei such as $^{18}$F, $^{13}$C, $^{23}$Na, $^{17}$O, $^{15}$N, or such as a metallic radioisotope (for example, $^{90}$Y, $^{177}$Lu, $^{64}$Cu, $^{99m}$Tc, $^{111}$In, $^{212}$Pb, $^{212}$Bi), the non-site specific method implements a chelating agent and comprises the following steps:

the conjugation of a chelating agent activated in the form of an ester or an anhydride, preferably in the form of an ester, with lysine residues of VHH, VHH variant or VHH derivative according to the invention, and the chelation of the ligand of step (i) with a substance of interest.

An alternative of the non-site specific method implementing a chelating agent is a method in which the substance of interest is "pre-chelated" with a chelating agent, such method comprising the following steps:

(i') the chelation of the substance of interest with a chelating agent activated in the form of an ester or an anhydride, preferably in the form of an ester, and (ii') the conjugation of the pre-chelated substance of interest of step (i') with lysine residues of VHH, VHH variant or VHH derivative according to the invention.

During the conjugation step (i) or (ii'), the temperature may vary from 1 to 40° C., and preferably from 4 to 20° C. The solution may be stirred from 1 to 6 hours. Preferably, the pH is maintained between 7 and 8.5 during the conjugation step (i) or (ii').

The conjugation step (i) or (ii') can be performed in PBS/NaCl with or without imidazole.

During the conjugation step (i) or (ii'), the chelating agent activated in the form of an ester or an anhydride may be dissolved in a buffer solution, such as a phosphate buffered saline (PBS) solution.

In a preferred embodiment, the molar ratio between the chelating agent activated in the form of an ester or an anhydride and the amino functions of the lysine residues of VHH, VHH variant or VHH derivative ranges from 1 to 10, and is preferably of 4.

Between the conjugation step (i) and the chelation step (ii), or between the chelation step (i') and the conjugation step (ii'), there may have a buffer exchange step by diafiltration or dialyse. Advantageously, the solution is diafiltrated, for example with a Vivaspin™ device. During this buffer exchange step, the medium is cooled at a temperature ranging from 1 to 5° C. During this buffer exchange step, the buffer solution is exchanged for example with a sodium acetate solution, preferably under stirring from 0 to 6 hours, and more preferably from 2 to 3 hours.

During the chelation step (ii) or (i'), the solution is stirred from 1 to 4 hours, preferably from 2 to 3 hours. The chelation step is preferably performed from 1 to 60° C., and more preferably at 4° C.

Then, there may have a second buffer exchange step by diafiltration or dialyse. Advantageously, the solution is diafiltrated, for example with a Vivaspin™ device. During this second buffer exchange step, the medium is cooled at a temperature ranging from 1 to 5° C. During this second diafiltration step, the buffer solution is exchanged for example with a mixture of PBS containing NaCl (PBS/NaCl; advantageously 300 mM NaCl), and may be concentrated by the same method (diafiltration).

Depending on the number of lysine, the substance of interest average density per VHH, VHH variant or VHH derivative may vary between 0 and the number of lysine+1. Preferably, the substance of interest average density per VHH, VHH variant or VHH derivative may vary between 0 and 6.

According to a second strategy, a VHH derivative of formula P-C-Z or Z-C-P according to the invention is conjugated to a substance of interest by using a site specific approach. The site specific approach has the following advantages:

the labeled VHH derivative of formula P-C-Z or Z-C-P is chemically-defined as this method affords well-defined conjugates which is an essential feature in the perspective of human use (quality control, safety . . . ), the method is easy and standard as the VHH derivative of formula P-C-Z or Z-C-P labeling with the substance of interest can be performed in a single step with short reaction time and straightforward procedure. There is no need for in-process monitoring and no trade-off to achieve between the labeling degree and the binding properties. These are key advantages for further optimization, experiment repeatability, and production scale-up, the method does not affect VHH derivative of formula P-C-Z or Z-C-P key properties: for instance, the pI of the conjugate is maintained above 8.5 which should allow for the BBB crossing. Furthermore, there is no remaining unlabeled VHH derivative of formula P-C-Z or Z-C-P which may compete with the conjugate for the target; the mild conditions with short reaction time at physiological pH prevent the VHH derivative of formula P-C-Z or Z-C-P from potential degradation and/or loss of activity, the method is versatile as it allows a flexible and modular approach where various VHH derivatives of formula P-C-Z or Z-C-P and contrast agents, fluorophores or other molecules of interest, can be prepared separately, and then combined in a single step. As a result, a set of conjugates are easily accessible for optimization and downstream evaluation by IHC (immunohistochemistry) and MRI (magnetic resonance imaging), and above all the method allows an improvement of the overall yield whilst reducing the number of steps reaction, without side reactions on the lysine or the histidine of the VHH, and with an overall maintenance of the function and the 3D structure of the VHH.

The site specific method according to the invention comprises a conjugation step of a VHH derivative of formula P-C-Z or Z-C-P according to the invention by thio-addition (conjugation step) with a thiol-reactive compound bearing a substance of interest, such as a maleimido compound of formula (I) or (I') as defined below bearing a substance of interest.

Whereas the non-site specific conjugation required an initial buffer exchange, the site-specific conjugation between the VHH, especially Tau-A2-SH or Tau-A2var-SH, and the thiol-reactive compound bearing a substance of interest can be implemented directly in a PBS/NaCl/imidazole buffer. Specific thio-addition on cystein could be efficiently controlled in mild conditions, said strategy allowing a reduction of the number of step reaction and an improvement of the overall yield of the process, without any of the potential side reactions previously mentioned in A. Papini et al., Int. J. Pept. Protein Res., 1992, 39, 348-355; B. Rudolf et al., J. Organomet. Chem, 1996, 522, 313-315; J. Paulech et al., Biochim. Biophys. Acta, 2013, 1834, 372-379.

Recombinant proteins are routinely expressed with a His-Tag which allows their purification by immobilized metal affinity chromatography (IMAC). When using a $Ni^{2+}$ nitrilotriacetic acid resin, they are typically eluted in a PBS buffer containing 500 mM imidazole. In the non-site specific approach, the nitrogens of the imidazole can promote the NHS ester hydrolysis (i.e. degrade the reactive species), and thereby interfere with the conjugation (G. T. Hermanson, Bioconjugate Techniques, Academic Press, 2013; P. Cuatrecasas et al., Biochemistry, 1972, 11, 2291-2299). A buffer exchange step must therefore be included in the process between the upstream affinity purification and the conjugation to remove the imidazole. Side-reaction between imidazole and maleimide groups are expected as previously reported by several groups showing the histidine side-chain alkylation (A. Papini et al.; B. Rudolf et al.; J. Paulech et al.). Nonetheless, the thiol-reactive compound bearing a substance of interest could be directly conjugated to the VHH, especially Tau-A2-SH or Tau-A2var-SH, in the affinity column elution buffer, with limited excess of maleimide reagent and despite a large molar excess of imidazole.

The thio-addition between the cystein of the VHH derivative of formula P-C-Z or Z-C-P and the thiol-reactive compound, such as the maleimido compound of formula (I) or (I') below, can be performed at a temperature ranging from 0 to 20° C., preferably 4° C., for instance from 2 to 4 hours.

The thio-addition between the cystein of the oligopeptide and the thiol-reactive compound such as the maleimido compound of formula (I) or (I') below is preferably realized at a pH ranging from 4 to 7.5, and more preferably at 6.8. Below pH=4, the reaction is not optimal, and above 7.5 the reaction is non specific (reaction on lysine). The conjugation step can be performed in PBS/NaCl with or without imidazole, and preferably in presence of imidazole.

Then, there may have a buffer exchange step by diafiltration or dialyse. Advantageously, the solution is diafiltrated, for example with a Vivaspin™ device. Then, the solution may be concentrated by the same method (diafiltration).

However, when the conjugation step is performed in PBS/NaCl with imidazole, it is preferable not to perform subsequent diafiltration or dialyse step (in order not to remove the imidazole).

Whether it is for the non-specific method or for the specific method, the substance of interest may be as defined above.

According to a preferred embodiment, the substance of interest is a therapeutic or diagnostic compound as defined above, preferably a diagnostic compound selected from the group consisting of fluorophore, radioisotope and NMR or MRI contrast agent as defined above.

The Inventors have observed that when the substance of interest is a fluorophore, or a NMR or MRI contrast agent, the synthesized conjugates retain the critical functional properties of the unlabeled VHH.

According to a preferred embodiment, the substance of interest is fluorophore, such as a green fluorescent dyes excited by blue light, in particular FITC, Cy2, Alexa Fluor® 488, preferably Alexa Fluor® 488.

According to another preferred embodiment, the substance of interest is a NMR or MRI contrast agent, such the paramagnetic agents gadolinium (Gd), dysprosium (Dy) and manganese (Mn), and the superparamagnetic agents based on iron oxides (such as MION, SPIO or USPIO) or iron platinium (SIPP), and X-nuclei such as $^{18}F$, $^{13}C$, $^{23}Na$, $^{17}O$, $^{15}N$, and more preferably the substance of interest is a NMR or MRI contrast agent selected from the paramagnetic agents gadolinium (Gd), dysprosium (Dy) and manganese (Mn), preferably gadolinium (Gd).

The chelating agent may be chosen among 1,4,7,10-tetraazacyclododecane-1,4,7,10-tetracetic acid (DOTA), diethylene triamine penta-acetic acid (DTPA), 1,4,7-tris (carboxymethylaza)cyclododecane-10-azaacetylamide (DO3A), nitrilotriacetic acid (NTA) (Chong et al. 2008 *Bioconjug Chem.*, 19, 1439-47), D-penicillamine (Pen), 2,3-dimercaptosuccinic acid (DMSA), 2,3-dimercapto-1- propanesulfonic acid (DMPS) (Andersen 1999 Chem Rev., 99, 2683-2710), 2,3-dimercaptopropanol (BAL), triethylenetetramine (Trien), the ammonium tetrathiomolybdate (TTM) anion (Brewer and Askari 2005 J Hepatol., 42, S13-S21), ethylenediaminetetraacetic acid (EDTA), 2-(p-isothiocyanatobenzyl)-6-methyl-diethylenetriaminepentaacetic acid (IB4M) (Nwe et al. 2011 J Inorg Biochem., 105, 722-7), hydroxypyridinone (HOPO) (Villaraza et al., 2010 Chem Rev., 110, 2921-59).

When the substance of interest is gadolinium, DOTA is the preferred chelating agent.

The present invention also provides a VHH derivative of formula P-C-Z or Z-C-P as defined above wherein said cystein residue C is linked to at least one substance of interest through a sulphide bond, preferably through a thio-ether or disulfide bond. Advantageously, said cystein residue C is linked to at least one substance of interest through a thiol-reactive compound bearing said substance of interest.

In the sense of the invention, a thiol-reactive compound is a maleimido, a haloacetyl, an alkyl halide or an aziridine compound, an acryloyl derivative, an arylating agent, or a thiol-disulfide exchange reagent (Hermanson G. T., 2010, Bioconjugate Techniques, Academic Press).

In the sense of the invention, a maleimido compound is a compound bearing at least one maleimide function, preferably from 1 to 6 maleimide functions, and more preferably one maleimide function.

Preferably, the thiol-reactive compound is a maleimido compound reacting with the cystein residue C through the C—C double bond of the maleimide function.

The maleimido compound of the invention may be of formula (I) as follows:

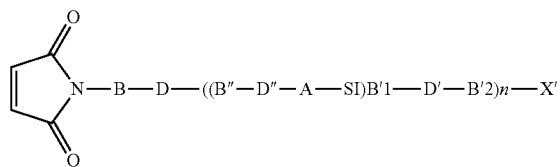

(I)

wherein:

B, B'$_1$, B'$_2$, and B", identical or different, are independently single bonds or spacers selected from polyols, such as polyethylene glycol (PEG) preferably having 2 to 12 oxyethylene (OE) units, polyolefins preferably having 2 to 12 aromatic rings, polyalkyls preferably having 2 to 12 carbon atoms, vinyl polymers such as poly(alkyl methacrylate) preferably having 2 to 12 methacrylate groups, polyaldehydes preferably having 2 to 12 carbonyl groups, polyacid esters preferably having 2 to 12 ester groups, D, D' and D", identical or different, are independently selected from amine, amide, amino-alcohol, urea, thiourea, carbamate, carbonate, ester, ether, thioether, aryl, heteroaryl such as triazole, oxime groups, A is a single bond or a chelating agent, SI is a substance of interest, X' is an acid, amine, amide, ester, ether, alkyl, alkenyl, alkynyl, aryl or heteroaryl function, and n=1 to 100, and preferably n=1, 2 or 3.

In the sense of the present invention:

Alkyl groups are chosen among ($C_1$-$C_{12}$)alkyl groups, and preferably ($C_1$-$C_6$)alkyl groups such as methyl, ethyl, n-propyl, isopropyl, n-butyl, sec-butyl, tert-butyl and isobutyl radicals;

Alkenyl groups are chosen among hydrocarbon chains of 2 to 12 carbon atoms, preferably 2 to 6, having at least one carbon-carbon double bond. Examples of alkenyl groups include ethenyl, propenyl, isopropenyl, 2,4-pentadienyl;

Alkynyl groups are chosen among hydrocarbon chains of 2 to 12 carbon atoms, preferably 2 to 6, having at least one carbon-carbon triple bond;

Aryl groups means any functional group or substituent derived from at least one simple aromatic ring; an aromatic ring corresponding to any planar cyclic compound having a delocalized π system in which each atom of the ring comprises a p-orbital, said p-orbitals overlapping themselves. More specifically, the term aryl includes, but is not limited to, phenyl, biphenyl, 1-naphthyl, 2-naphthyl, anthracyl, pyrenyl, and the substituted forms thereof. The aryl groups of the invention comprise preferably 4 to 12 carbon atoms, and more preferably 5 or 6 carbon atoms;

Heteroaryl groups means any functional group or substituent derived from at least one aromatic ring as defined above and containing at least one heteroatom selected from P, S, O and N. The term heteroaryl includes, but is not limited to, furan, pyridine, pyrrole, thiophene, imidazole, pyrazole, oxazole, isoxazole, triazole, thiazole, isothiazole, tetrazole, pyridazole, pyridine, pyrazine, pyrimidine, pyridazine, benzofurane, isobenzofurane, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine. The aryl and heteroaryl groups of the invention comprise preferably 4 to 12 carbon atoms, and more preferably 5 or 6 carbon atoms;

The acid, amine, amide, ester, ether and thioether groups according to the invention have preferably 1 to 12, and more preferably 1 to 6 carbon atoms.

According to a preferred embodiment, A is a chelating agent and the substance of interest SI is a fluorophore (e.g., Alexa Fluor® 488) or a NMR or MRI contrast agent (e.g., gadolinium).

Advantageously, the chelating agent A is selected from 1,4,7,10-tetraazacyclododecane-1,4,7,10-tetracetic acid (DOTA), diethylene triamine pentaacetic acid (DTPA), 1,4,7-tri s(carboxymethylaza)cyclododecane-10-azaacethylamide (DO3A), nitrilotriacetic acid (NTA), D-penicillamine (Pen), 2,3-dimercaptosuccinic acid (DMSA), 2,3-dimercapto-1-propanesulfonic acid (DMPS), 2,3-dimercaptopropanol (BAL), triethylenetetramine (Trien), the ammonium tetrathiomolybdate (TTM) anion, ethylenediaminetetraacetic acid (EDTA), 2-(p-isothiocyanatobenzyl)-6-methyl-diethylenetriaminepentaacetic acid (IB4M) or hydroxypyridinone (HOPO).

Advantageously, the substance of interest SI is gadolinium, and the chelating agent is DOTA.

According to a particularly preferred embodiment, the maleimido compound of the invention may be of formula (I'):

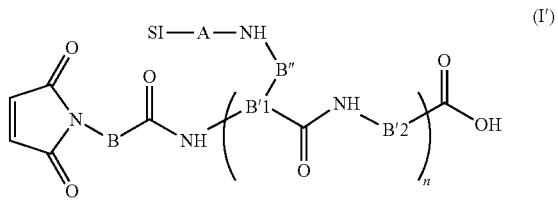

(I')

wherein B, B'$_1$, B'$_2$, B", A, SI and n are as defined above.

The maleimido compound of formula (I) or (I') may be synthesized through a solid-phase method, preferably using Fmoc chemistry, and more preferably on a Fmoc-Gly-Wang resin.

According to a preferred embodiment, the maleimido compound of the invention may be of formula (I'):

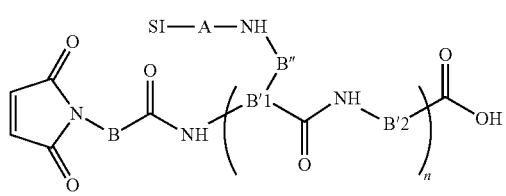

wherein B, B'$_1$, B'$_2$, B", A, SI and n are as defined above is also part of the invention.

Another object of the invention is a VHH derivative of formula P-C-Z or Z-C-P as defined above with a cystein residue linked to at least one substance of interest (e.g., a fluorophore such as Alexa Fluor 488 or a NMR or MRI contrast agent such as gadolinium), and preferably linked to at least one substance of interest through a thiol-reactive compound, and more preferably a maleimido compound as defined according to the invention, said VHH derivative of formula P-C-Z or Z-C-P being obtainable according to the site specific method of the invention.

The present invention also provides a VHH or VHH variant conjugated to a substance of interest obtainable according to the non-site specific method of the invention, and also a VHH derivative of formula P-C-Z or Z-C-P conjugated to a thiol-reactive compound such as a maleimido compound of formula (I) bearing a substance of interest obtainable according to the site specific method of the invention.

If the substance of interest is a peptide, then the VHH, VHH variant or VHH derivative according to the present invention and said substance of interest can be produced by genetic engineering as a fusion polypeptide that includes the VHH, VHH variant or VHH derivative according to the invention and the suitable peptide. This fusion polypeptide can conveniently be expressed in known suitable host cells.

The VHH, the VHH variant, the VHH derivative, the therapeutic or diagnostic agent, according to the present invention can be administered to a subject (a mammal or a human) by injection, such as intravenous, intraarterial, intrathecally (via the spinal fluid), intraperitoneal, intramuscular or subcutaneous injection, or by intranasal instillation.

When the VHH, VHH variant or VHH derivative according to the present invention is administered to a human subject, then it can be humanized in order to reduce immunogenicity in human. Methods for producing humanized antibodies or fragments thereof are known in the art (Vincke et al. 2009, *J Biol Chem.*, 284, 3273-84).

A diagnostic agent according to the present invention can be used in brain imaging, in diagnosing or monitoring a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP.

The present invention also provides a kit comprising a VHH, a VHH variant or a VHH derivative (in particular a VHH derivative of formula P-C-Z or Z-C-P) according to the present invention and a substance of interest as defined above, and optionally a diagnostic reagent.

The present invention also provides a kit comprising a diagnostic agent according to the present invention and a diagnostic reagent.

The kits according to the present invention can be used for brain imaging, or for diagnosing or monitoring a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP.

The present invention also provides the use of a diagnostic agent according to the present invention for diagnosing or monitoring a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP, in a subject.

As used herein, a "subject" is a mammal, preferably a human, and most preferably a human suspected of having a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP.

The present invention also provides an in vitro or ex vivo method for diagnosing a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP, in a subject, comprising the steps of:

a) contacting in vitro an appropriate biological sample from said subject with a diagnostic agent according to the present invention, and b) determining the presence or the absence of phosphorylated-tau protein in said biological sample, the presence of said phosphorylated-tau protein indicating that said subject has a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP.

Step b) can be carried out by determining the presence or the absence of the VHH-antigen or VHH variant-antigen complex (i.e., VHH directed to a phosphorylated-tau protein).

The present invention also provides an in vitro or ex vivo method for monitoring the progression or regression of a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP, in a subject, comprising the steps of:

a) contacting in vitro an appropriate biological sample from said subject with a diagnostic agent according to the present invention, b) determining the amount of phosphorylated-tau protein in said biological sample, and c) comparing the amount determined in step (b) with the amount of phosphorylated-tau protein previously obtained for said subject, a significant increase in amount of phosphorylated-tau protein constituting a marker of the progression of said disorder mediated by neurofibrillary tangles, neuropil threads or dystrophic neurites, and a significant decrease of phosphorylated-tau protein constituting a marker of the regression of said disorder mediated by neurofibrillary tangles, neuropil threads or dystrophic neurites.

As used herein the terms "significant increase" and "significant decrease" refer to a higher amount or lower amount respectively of phosphorylated-tau protein in an appropriate biological sample with respect to the amount of phosphorylated-tau protein in an appropriate biological sample from said subject, that was previously determined and used as a reference amount.

Step b) can also be carried out by determining the amount of the VHH-antigen or VHH variant-antigen complex.

Said appropriate biological sample can be a brain biopsy or post-mortem brain tissue.

According to the aspect of the invention which relates to a method of detecting neurofibrillary tangles, neuropil threads or dystrophic neurites in brain biopsy or post-mortem brain tissue, the method may involve incubating formalin-fixed tissue with a solution of a diagnostic agent according to the invention. Upon incubation, the diagnostic compound labels the neurofibrillary tangles, neuropil threads or dystrophic neurites in the tissue, and the stained or labeled neurofibrillary tangles, neuropil threads or dystrophic neurites can be detected or visualized by any standard method. Such detection means include microscopic techniques such as bright-field, fluorescence, laser-confocal and cross-polarization microscopy. The method of quantifying the amount of neurofibrillary tangles, neuropil threads or dystrophic neurites in biopsy or post-mortem tissue involves, for example incubating a diagnostic agent according to the present invention, or a water-soluble, non-toxic salt thereof, with homogenate of biopsy or post-mortem tissue. The tissue is obtained and homogenized by methods well known in the art. Advantageously the diagnostic compound is a radioisotope-labeled compound, although other diagnostic compounds such as enzymes, fluorophores, nanoparticles or NMR or MRI contrast agents can be used.

The present invention also provides a method for in vivo imaging neurofibrillary tangles, neuropil threads or dystrophic neurites in a subject comprising the steps of:

a) administrating a detectable quantity of a diagnostic agent according to the present invention in a subject, preferably a human and, b) detecting the diagnostic agent in said subject by an imaging method.

This method according to the present invention allows determining the presence and location of neurofibrillary tangles, neuropil threads or dystrophic neurites in brain of a subject, preferably a human.

As used herein a "detectable quantity" means that the amount of the diagnostic agent that is administered is sufficient to enable detection of binding of the diagnostic agent to phosphorylated-tau protein.

As used herein an "imaging effective quantity" means that the amount of the diagnostic agent that is administered is sufficient to enable imaging of binding of said diagnostic agent to phosphorylated-tau protein.

Imaging methods include non-invasive neuroimaging techniques such as magnetic resonance spectroscopy (MRS) or imaging (MRI), or gamma imaging such as positron emission tomography (PET) or single-photon emission computed tomography (SPECT), used to detect neurofibrillary tangles, neuropil threads or dystrophic neurites in vivo.

For purposes of in vivo imaging, the type of detection instrument available is a major factor in selecting a given label. For instance, gadolinium, iron or manganese based contrast agents can be used to detect the VHH, VHH variant or VHH derivative according to the present invention linked to said substances of interest by magnetic resonance spectroscopy (MRS) or imaging (MRI). Radioactive isotopes such as $^{19}$F, fluorophores such as Alexa Fluor® 488 or NMR or MRI contrast agent such as gadolinium are also particularly suitable for in vivo imaging in the methods of the present invention. The type of instrument used will guide the selection of the substances of interest. For instance, the radionucleotide chosen must have a type of decay detectable by a given type of instrument. Another consideration relates to the half-life of the contrast agent or radionuclide. For radioisotopes, the half-life should be long enough so that it is still detectable at the time of maximum uptake by the brain, but short enough so that the subject does not sustain deleterious radiation. The radiolabeled VHH, VHH variant or VHH derivative according to the present invention can be detected using gamma imaging wherein emitted gamma irradiation of the appropriate wavelength is detected. Methods of gamma imaging include, but are not limited to, SPECT and PET. Preferably, for SPECT detection, the chosen radioisotope will lack a particulate emission, but will produce a large number of photons in a 140-200 keV range. For PET detection, the radiolabel will be a positron-emitting radionuclide such as $^{19}$F which will annihilate to form two 511 keV gamma rays which will be detected by the PET camera.

Generally, the dosage of the detectable diagnostic agent will vary depending on considerations such as age, condition, sex, and extent of disorder in the patient, contraindications, if any, concomitant therapies and other variables, to be adjusted by a physician skilled in the art. Administration to the subject may be local or systemic and accomplished intravenously, intraarterially, intrathecally (via the spinal fluid) or the like. Administration may also be intradermal or intracavitary, depending upon the body site under examination. After a sufficient time has elapsed for the compound to bind with the phosphorylated tau protein, for example 30 minutes to 48 hours, the area of the subject under investigation is examined by routine imaging techniques such as MRS/MRI, SPECT, planar scintillation imaging, PET, and any emerging imaging techniques, as well. The exact protocol will necessarily vary depending upon factors specific to the patient, as noted above, and depending upon the body site under examination, method of administration and type of label used; the determination of specific procedures would be routine to the skilled artisan.

The present invention also provides a VHH, VHH variant or a VHH derivative according to the invention, in particular a VHH derivative of formula P-C-Z or Z-C-P, linked to a diagnostic compound according to the present invention as a diagnostic agent.

The present invention also provides a pharmaceutical composition comprising a therapeutic agent as defined above and a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

The present invention also provides a VHH, a VHH variant, a VHH derivative, a therapeutic agent or a pharmaceutical composition according to the present invention as a medicament, in particular for use in the treatment of a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP.

The present invention also provides a method for preventing or treating a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP, comprising administering to a subject in need thereof a therapeutic agent or a pharmaceutical composition according to the present invention.

As used herein, the terms "treatment" or "treating" includes the administration of the VHH, the VHH variant, the VHH derivative, the therapeutic agent or the pharmaceutical composition according to the present invention to a patient who has a disorder, a symptom of disorder or a predisposition toward a disorder, with the purpose to cure, heal, alleviate, relieve, alter, remedy, ameliorate, improve or affect the disorder, the symptoms of the disorder, or the predisposition toward disorder.

The term "preventing" means that the progression of a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP, is reduced and/or eliminated, or that the onset of a disorder mediated by neurofibrillary tangles, neuropil threads or dystrophic neurites, such as tauopathies, including Alzheimer's disease (AD), Pick disease (PD), fronto-temporal dementia (FTD), corticobasal degeneration (CBD) and progressive supranuclear palsy (PSP), preferably AD, FTD, CBD and PSP, is delayed or eliminated.

In another aspect, the present invention relates to the use of a VHH, a VHH variant or a VHH derivative according to the invention, in particular a VHH derivative of formula P-C-Z or Z-C-P, for the preparation of a peptide vector for delivering a substance of interest as defined above across a mammal blood-brain, preferably a human blood-brain barrier.

The present invention also provides a VHH derivative of formula P-C-Z or Z-C-P linked to a therapeutic compound according to the present invention as a therapeutic agent.

In addition to the preceding features, the invention further comprises other features which will emerge from the following description, which refers to examples illustrating the present invention, as well as to the appended figures.

BRIEF DESCRIPTION OF THE DRAWINGS

FIGS. 11A to 11D show the biochemical and histological characteristics of Tau-A2 variant. A: Protein profile analysis of VHH Tau-A2-SH (left) and Tau-A2var-SH (right) by instant Blue stained SDS-PAGE gel. B: Determination of pI of Tau-A2-SH (lane 1) and Tau-A2var-SH (lane 2) by NEPHGE on 3-10 IEF gel. C: ELISA Binding of VHH Tau-A2-SH and VHH Tau-A2var-SH on coated Phospho-Tau protein. A negative control was performed by using an irrelevant VHH. The VHH binding was revealed by the addition of a mouse anti-His tag mAb revealed by an anti-mouse antibody labelled with peroxydase D: Comparison of VHH Tau-A2-SH and VHH Tau-A2var-SH by IHC on Tg4510 mice. VHH were used at the concentration of 2 µg/ml and their presence was revealed by anti-His mouse mAb followed by a peroxydase labelled anti-mouse-Ig.

EXAMPLE I

Figure 1:
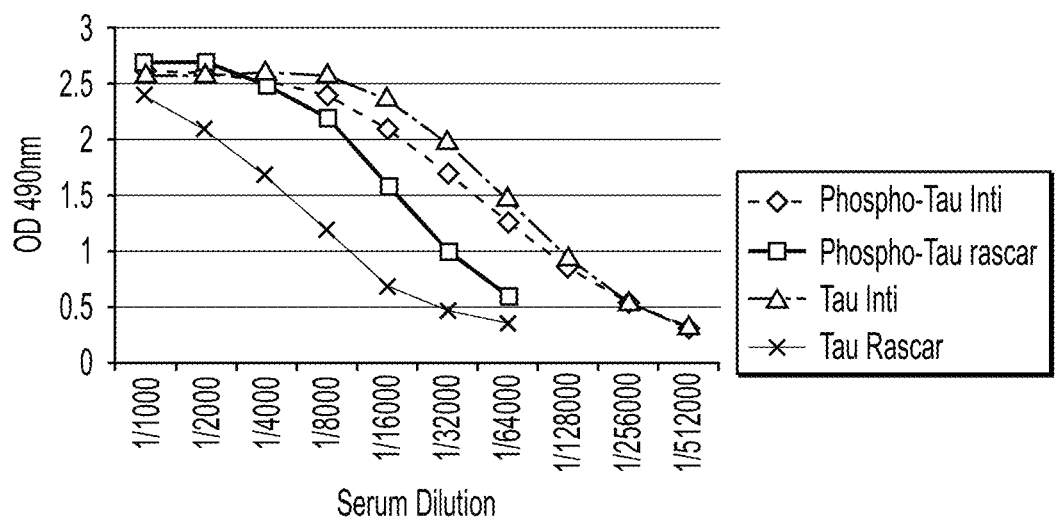
FIG. 1 shows the binding of Inti and Rascar sera against phospho-tau and tau proteins. The alpaca polyclonal antibodies were detected with rabbit anti-alpaca antibodies.

Generation of Anti-Phosphorylated Tau VHHS Coupled to Alexa Fluor®488 or Gadolinium Contrast Agent and Their Evaluation In Vitro/In Vivo Materials and Methods
1. Production, Selection and Purification of Anti-Tau Specific VHH (Tau-A2)
1.1 Antigen Preparation and Induction of a Humoral Immune Response in Alpaca
Subjects Human cortical brain tissues from AD patients (Braak stage V and VI) were obtained from the NeuroCEB brain bank. This bank is associated to a brain donation program run by a consortium of patients associations (including France Alzheimer Association) and declared to the French Ministry of Research and Universities, as requested by French Law. An explicit written consent was obtained for the brain donation in accordance with the French Bioethical Laws.

Tissue extraction was performed according to Mercken et al. (1992 *Acta Neuropathol.*, 84, 265-272). Cortex from AD brain (0.2 g) was homogenized in 10 volumes of 10 mM Tris, 1 mM EGTA, 0.8 M NaCl pH7.4 containing 10% sucrose and was centrifuged at 27,000×g for 20 min at 4° C. The pellet was removed and the supernatant was adjusted to 1% N-laurylsarcosine and 1% beta-mercaptoethanol and incubated while rotating for 2.5 hours at 37° C. The supernatant mixture was centrifuged at 100,000 g for 35 min at 20° C. The PHF containing pellet was gently washed with PBS and finally resuspend in the same buffer.

One alpaca (Inti) was immunized with tau pellet and another alpaca (Rascar) was immunized with the single phospho-peptide derived from the C-terminus of a tau protein of sequence CSIDMVDS(PO$_3$H$_2$)PQLATLAD (SEQ ID NO. 6), coupled to KLH (Eurogentec).

250 µl (500 µg) of both antigens was mixed with 250 µl of Freund complete adjuvant for the first immunization, and with 250 µl of Freund incomplete adjuvant for the following immunizations. After three immunizations at day 0, 21 and 40, a serum sample was taken at day 52 and the immune response monitored by ELISA using recombinant phospho-tau protein or recombinant non-phosphorylated tau protein.

1.2 Library Construction and Panning
250 ml of blood of the immunized animals was collected at day 52 and the peripheral blood lymphocytes isolated by centrifugation on a Ficoll (Pharmacia) discontinuous gradient and stored at −80° C. until further use. Total RNA and cDNA was obtained as previously described in Lafaye P. et al. (1995 *Res Immunol.*, 146, 373-382), and DNA fragments encoding VHH domains amplified by PCR using CH2FORTA4 and VHBACKA6 primers, which anneal to the 3' and 5' flanking region of the VH genes, respectively. The amplified product was used as template in a second round of PCR using either of the primers VHBACKA4 and VHFOR36. The primers were complementary to the 5' and 3' ends of the amplified product and incorporated SfiI and NotI restriction sites at the ends of the VHH genes. The PCR products were digested and ligated into phage expression vector pHEN1. The resulting library was composed of two sub-libraries, one derived from tau pellet and the other from phospho peptide coupled to KLH. Phages were produced and isolated using both sub-libraries, and subsequently pooled.

The library (>6×10$^8$ clones) was panned against full-length phospho-tau protein. Nunc Immunotubes (Maxisorp) tubes were coated overnight at 4° C. with the antigen (10 µg/ml) in PBS. Phages (10$^{12}$ transducing unit) were panned by incubation with the coated tubes for 1 h at 37° C. with gentle agitation. A different blocking agent was used at each of the three rounds of panning: 2% skimmed milk, Licor blocking buffer (Biosciences) diluted 1:4, and 4% BSA were respectively used. Phage clones were screened by standard ELISA procedures using a HRP/anti-M13 monoclonal antibody conjugate (GE Healthcare) for detection (see below). The screening was performed in parallel with phospho-tau protein and tau protein.

1.3 Expression of VHHs
The coding sequence of the selected nanobodies in vector pHEN1 was sub-cloned into a bacterial expression vector pET23d containing a 6-Histidine tag using NcoI and NotI restriction sites. Transformed *E. coli* BL21 (DE3) pLysS cells express VHH in the cytoplasm after overnight induction with IPTG (0.5 mM) at 16° C. Purified VHHs were isolated by IMAC from cytoplasmic extracts using a HiTrap crude column charged with Ni$^{2+}$ (GE Healthcare), according to the manufacturer's instructions. The VHHs were eluted in 50 mM sodium phosphate buffer, 300 mM NaCl and 500 mM imidazole buffer and dialyzed in PBS buffer containing 300 mM NaCl (PBS/NaCl).

The coding sequence of selected VHHs was also sub-cloned into a modified pASK IBA2 expression vector containing a Strep-tag at C-ter end (Skerra and Schmidt 1999 *Biomol Eng.*, 16, 79-86). Same restriction sites were used. *E. coli* XL2-Blue Ultracompetent cells were transformed to express VHHs in the periplasm after overnight induction with anhydrotetracycline (AHT, 200 µg/l) at 16° C. VHHs were then purified from bacterial extract with Strep-Tactin column (IBA) according to manufacturer's instructions.

2. VHH Tau-A2 Coupling to MRI Contrast Agents and to Fluorophores
2.1 General Synthesis Methods Unless otherwise specified, the amino-acid derivatives and the reagents were purchased from Novabiochem and Sigma-Aldrich, respectively. The concentration of the peptide and VHH solutions (net protein content) was determined by quantitative amino acid analysis (AAA) using a Beckman 6300 analyzer after hydrolysis of the compounds with 6N HCl at 110° C. for 20 hours. The RP-HPLC/MS analyses were performed on an Alliance 2695 system coupled to a UV detector 2487 (220 nm) and to a Q-Tof-micro™ spectrometer (Micromass) with an electrospray ionisation (positive mode) source (Waters). The samples were cooled to 4° C. on the autosampler. The linear gradient was performed with acetonitrile+0.025% formic acid (A)/water+0.04% TFA+0.05% formic acid (B) over 10 or 20 min. The column used was a XBridge™ BEH300 C18 (3.5

µm, 2.1×100 mm) (Waters) (gradient 10-100% A). The source temperature was maintained at 120° C. and the desolvation temperature at 400° C. The cone voltage was 40 V. The samples were injected at 0.4-1 mg/ml concentration in their respective buffer added with B.

Figure 6:
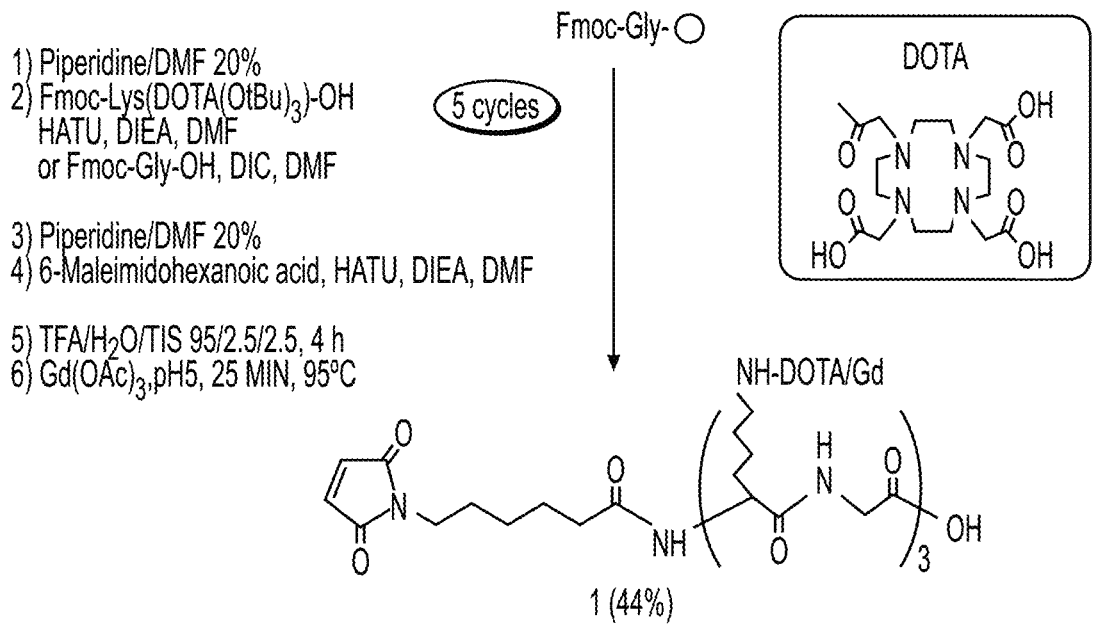
FIG. 6 shows the solid-phase synthesis of maleimido-(DOTA/Gd)$_3$ (compound 1).

A maleimido-(DOTA/Gd)$_3$ compound 1 was prepared by solid-phase peptide synthesis using 9-fluorenylmethoxycarbonyl (Fmoc) chemistry as shown in FIG. 6.

2.2 Production of Tau-A2-SH

The coding sequence of a Cys-engineered VHH (Tau-A2-SH) was cloned into a bacterial expression vector pET23d using NcoI and XhoI restriction sites. To summarize, Tau-A2-SH (SEQ ID NO. 14) comprises from the N to the C terminus a 6-Histidine tag, a thrombin cleavage site, VHH Tau-A2 sequence followed by a G3 S spacer and three extra amino acids CSA. Transformed E. coli BL21 (DE3) pLysS cells express Tau-A2-SH in the cytoplasm after overnight induction with IPTG (0.5 mM) at 16° C. Purified VHHs were isolated by IMAC from cytoplasmic extracts using a HiTrap crude column charged with Ni2+ (GE Healthcare), according to manufacturer's instructions. The protein was eluted in PBS/NaCl containing 500 mM imidazole and then dialyzed in PBS/NaCl.

AAA: Ala 14.3 (14), Arg 9.6 (10), Asp+Asn 7.3 (6), Glu+Gln 11.2 (10), Gly 18.4 (19), His 5.7 (6), Ile 4.2 (4), Leu 8.6 (8), Lys 5.3 (5), Phe 4 (4), Pro 2.9 (2), Ser 18.9 (23), Thr 10.5 (12), Tyr 6.1 (7), Val 11.5 (11).

MS: 15499.286 (C669H1047N205O213S4 calculated 15498.190). The MS corresponds to the protein with N-ter deleted methionine.

2.3 Synthesis of Tau-A2-S-Alexa Fluor® 488 (Tau-A2-S-AF488)

The cysteine present in the C-ter tripeptide of Tau-A2-SH was used to couple the Tau-A2-SH to the maleimido Alexa Fluor® 488 fluorophore (Invitrogen). pH of the solution containing Tau-A2-SH was adjusted between 6.8 and 7. The solution was then gently stirred with 10-fold molar excess of tris(2-carboxyethyl) phosphine (TCEP) at room temperature for 30 min, to allow complete reduction of any intermolecular disulfide bond. A 10-fold molar excess of maleimido Alexa Fluor® 488 fluorophore dissolved in dimethylformamide (DMF) was added. Notably, for high efficiency of conjugation, the volume percentage of DMF in the final solution was kept below 5%. The conjugation was performed for 2 hours at room temperature, under protection from light. The non-conjugated maleimido fluorophore was then removed by successive dialysis with PBS containing 300 mM NaCl (overall concentration).

2.4 Synthesis of Tau-A2-S-(DOTA/Gd)$_3$

Prior to the conjugation, Tau-A2-SH (4.2 ml, 0.32 mg/ml in PBS/NaCl pH 6.8) was treated with TCEP (24.6 µg, 5 eq) for 30 min to prevent the dimerization of the VHH. Maleimido-(DOTA/Gd)$_3$ (0.78 mg, 3.8 eq relative to 1 thiol group per VHH) in aqueous solution (78 µl) was added to the protein and the solution was stirred at 4° C. for 3 h. The solution was then dialyzed in PBS/NaCl using Slide-A-Lyzer cassettes (Thermo Scientific) (3,500 MWCO). Aliquots (20 µl) of Tau-A2-SH and Tau-A2-S-(DOTA/Gd)$_3$ were diluted with buffer B (20 µl) for RP-HPLC/MS analyses. Further, aliquots (10 µl) of the same compounds were diluted in 20 mM Tris buffer pH 7.3 (90 µl) for ELISA analyses. 4.2 ml of Tau-A2-S-(DOTA/Gd)$_3$ (0.24 mg/ml) was obtained with a yield of 65%. It was calculated by dividing the actual amount of the final product Tau-A2-S-(DOTA/Gd)$_3$ by its expected amount (net protein contents). For further experiments, the solution of Tau-A2-S-(DOTA/Gd)$_3$ was concentrated four times using Vivaspin 2 centrifugal filter device (3,000 MWCO PES).

AAA: Ala 13.4 (14), Arg 9.6 (10), Asp+Asn 8.0 (6), Glu+Gln 11.8 (10), Gly 24.4 (22), His* (6), Ile 4.2 (4), Leu 8.6 (8), Lys 18.9* (8), Phe 4 (4), Pro 2.9 (2), Ser 16.8 (23), Thr 10.7 (12), Tyr 6.1 (7), Val 11.4 (11). [*His cannot be determined due to co-elution with ammonium. Lys is overestimated due to co-elution with maleimido derivative in the conditions of the analysis.].

MS: 17887.549 (C751H1174N227O244S4Gd3 calculated 17886.980).

3. In Vitro Characterization of Tau-A2, and Tau-A2 Conjugates by Immunohistochemistry and Biochemistry 3.1 Subjects Human brain tissue was obtained from the NeuroCEB brain bank. Preclinical experiments were performed on Tg4510 (Santacruz et al. 2005 *Science*, 309, 476-81) transgenic mice. Animal experimental procedures were performed in strict accordance with the ethical standards of French and European laws (European Communities Council Directive 2010/63/EU on the protection of animals used for scientific purposes) and after approval from local Animal Care and Use committee. The animals were sacrificed using a high dose of sodium pentobarbital (100 mg/kg) and then perfusion-fixed with 10% buffered formalin. Their brains were then removed, immersed in formalin for at least 24 hours and stored at 4° C.

3.2 Tissue Extracts

Tissue extraction was performed according to Mercken et al. (1992 *Acta Neuropathol.*, 84, 265-272).

3.3 Immunoblots

Phospho-tau protein was resuspended in NuPAGE® LDS sample buffer (Invitrogen). Brain extracts were resuspended in NuPAGE® LDS sample buffer (Invitrogen) containing 8 M urea. Following separation by polyacrylamide gel electrophoresis (PAGE) using NuPAGE Novex 4-12% Bis-tris gel (Invitrogen), semi-dry transfer onto Hybond-C (Amersham) and western blotting were carried out using the Xcell II blot module (Invitrogen). Prior to the immunochemical reaction, membranes were blocked in a 4% skimmed milk solution. Immunoblotting of membranes was accomplished with VHH (with His or Strep tag) or anti p-tau 422 mAb (Grueninger et al. 2011 *Mol Cell Biochem.*, 357, 199-207) and revealed by rabbit anti-His tag (eBioscience) polyclonal antibodies followed by peroxidase labeled goat anti-rabbit immunoglobulins (Abcam) or by an anti-Strep tag monoclonal antibody (such as the antibody C23-21 produced by the hybridoma filed with the CNCM under the number 1-4703) followed by peroxidase labeled rabbit anti-mouse immunoglobulins (Bio-rad). Finally, peroxidase activity was visualized using a chemiluminescent kit (GE Healthcare).

3.4 ELISA

Microtiter plates (Nunc, Denmark) were coated by incubation overnight at 4° C. with 1 µg/ml of phospho-tau or tau protein or the phospho-peptide of SEQ ID NO. 6 coupled to ovalbumine protein diluted in PBS. Plates were washed with buffer 0.1% Tween 20 in PBS. Tau-A2 (with His or Strep tag) was diluted in buffer 0.5% gelatin 0.1% Tween 20 in PBS. After 2 h incubation at 37° C., plates were washed again before adding respectively a rabbit anti-His tag polyclonal antibody (eBiosciences), followed by peroxidase labeled goat anti-rabbit immunoglobulins (Abcam) or by an anti-Strep tag monoclonal antibody (such as the antibody C23-21) followed by peroxidase labeled rabbit anti-mouse immunoglobulins (Bio-rad), and finally revealed by OPD (o-phenylendiamine dihydrochloride, Dako) according to manufacturer's protocol.

3.5 Sequences Analysis

VHH encoded DNAs were sequenced by GATC Biotech and sequences were treated with Serial Cloner.

3.6 Determination of pI

The pI of VHHs was determined by isoelectric focusing using IEF 2-9 Gel (Invitrogen). NEPGHE (non equilibrium pH gradient gel electrophoresis) with sample application at the anode because it allows optimal protein analysis in the basic range of the gel including pH 8.5 to 10.5. The protocol was detailed in SERVAGel IEF 3-10 instruction manual.

3.7 Immunohistochemistry and Immunofluorescence

Immunohistochemistry was performed on formalin-fixed tissues (paraffin-embedded or frozen sections or vibratome sections). Standard IHC protocols were applied and adapted for each tissue conditions. As most of immunostaining experiments were performed using paraffin sections, a detailed protocol for paraffin-embedded material is described herein. Immunostaining of brain tissue was performed on 4 µm thick paraffin sections. Both human and mouse tissues were used (Human patients with AD or other tauopathies and Tg4510 mice (Santacruz et al. 2005 Science, 309, 476-481). Sections were de-paraffinized in xylene, rehydrated through ethanol (100%, 90%, and 70%), 5 min for each solution and finally brought to running tap water for 10 min. They were then incubated in 98% formic acid for 5 min, washed again under running tap water, quenched for endogenous peroxidase with 3% hydrogen peroxide and 20% methanol, and finally washed in water. Non-specific binding was blocked by incubating the sections for 30 min in 2% bovine serum albumin in TBS+0.5% Tween. Appropriate dilutions of primary antibodies (1-10 µg/ml of VHH with either His or Strep tag) were then applied and slices incubated overnight in a humidified chamber at 4° C. Slides were washed with TBS-Tween and incubated with secondary antibodies rabbit anti-His Tag for 1/1000 or home-made biotinylated anti-strep mAb C23-21 in TBS-Tween at room temperature for 1 hour. Slides were then incubated with reagents of Dako REALTM Detection System, Peroxidase/DAB+ according to manufacturer's instructions. Chromogenic (DAB) revelation was developed until a good signal-to-noise ratio was obtained (about 5 min). After washing with TBS-Tween, slides were counter-stained with hematoxylin. For labeling of NFTs, biotinylated mAb AT8 (ThermoScientific) was used as a positive control in parallel.

Immunofluorescent staining of NFTs using Tau-A2-S-AF488 was performed on 40 µm thick free floating sections obtained from Tg4510 mice using vibratome (Leica VT1000S). After 3×5 min washing in PBS, sections were blocked by incubating for 15 min with PBS-triton 0.2% containing 2% of BSA, which was then replaced by 1 µg/ml of Tau-A2-S-AF488 in PBS-triton 0.2% and incubated overnight at 4° C. Sections were finally washed with PBS and mounted with an aqueous mounting medium (Mowiol).

4. In Vivo Evaluation of Tau-A2 and Tau-A2 Conjugates by Two-Photon Imaging and Correlative Immunohistochemistry 4.1 Subjects In vivo evaluation of Tau-A2, and Tau-A2-S-(DOTA/Gd)$_3$ was performed on Tg4510 transgenic mice.

4.2 Stereotaxic Injection of VHH and IHC

Stereotaxic injections were performed in Tg4510 female transgenic mice (n=2) anesthetized mice with 2 µl of VHH per injection at the rate of 0.5 µl/min. The mice were anesthetized with a mixture of isoflurane (1-2%) and air (1 l/min). They were placed on a stereotaxic frame and the skull was bilaterally perforated with a Dremel. Blunt Hamilton syringes were used to inject MRI contrast agent. Each mouse received 4 injections, in the frontal cortex and the hippocampus in each hemisphere. The stereotaxic coordinates in the frontal cortex were +0.86 mm anterior from bregma, ±1.5 mm lateral from the midline, −0.65 mm ventral from dura. The stereotaxic coordinates in the hippocampus were −2.18 mm posterior from bregma, ±1.5 mm lateral from the midline, −1.8 mm ventral from dura. Two or 24 hours after the injection, mice were euthanized and perfused intracardially with 4% paraformaldehyde in PBS (pH 7.6). Brains were removed and post-fixed in the same fixative overnight at 4° C. 4 µm thick paraffin sections were prepared. The presence of the VHH in cerebral tissue was detected using immunohistochemical procedures described above.

4.3. Two Photon Microscopy in Tg4510 Mice Using Tau-A2-S-AF488

1) Craniotomy

Two 8-month-old Tg4510 mice were anesthetized by inhalation of isoflurane (1% vol/vol in pure $O_2$) and placed onto a warming blanket (37° C.). A stereotaxic frame was used to identify the location of the motor cortex. 50 µl of 2% lidocaine was injected subcutaneously for local anesthesia at the incision site location where the skin was to be removed. A less than 2 mm craniotomy was performed using a scalpel. In the case of intracerebral injections of VHH Tau-A2-S-AF488, the dura mater was incised. In the case of intravenous injections, the dura mater was kept intact. To avoid movement artifacts, the skull opening was covered with 2% low melting point agarose and a coverglass. The optical window was secured and sealed to skull with dental cement, covering all the exposed skull, wound margins and coverglass edges.

2) Administration of Tau-A2-S-AF488

Intracerebral injection: 1.2 µg (1.5 µL) of Tau-A2-S-AF488 was injected in the brain of one Tg4510 mouse at 1.5 mm depth from cortical surface. Two-photon imaging was then performed during 4 h after injection.

Intravenous injection: 270 µg (150 µl) of Tau-A2-S-AF488 was slowly injected into the caudal vein of one Tg4510 mouse. Two-photon imaging was then performed in the following 3 hours.

3) Two-Photon Imaging

Two-photon imaging was performed with a two-photon laser-scanning microscope system and PrairieView software (Prairie Technologies, Middelton, Wis., USA), using a 16×0.9 NA water immersion objective (Nikon, Tokyo, Japan) with the 2-photon laser tuned to 920 nm (MaiTai DeepSee, Spectra Physics, Mountain View, Calif., USA). The images were acquired at 512×512 with a pixel size of 0.5 µm. Care was taken to use less than 20 mW of laser power in the tissue.

5. Obtention of Rabbit Polyclonal Anti-VHH Antibodies

Purified alpacas immunoglobulins were used to immunize one rabbit. Rabbit polyclonal antibodies against VHH were purified in 2 steps. First polyclonal antibodies were isolated by immunochromatography using protein A-sepharose 4B beads. Then another immunochromatography was realized by using sepharose 4B beads labelled with Tau-A2var-SH. The sepharose labelling was realized according to manufacturer's instructions (GE). The resulting purified antibodies represented less than 1% of total rabbit antibodies and are referred to as rabbit polyclonal anti-VHH antibodies. These antibodies bind to Tau-A2 VHH.

Results

1. Polyclonal Response, Library Construction, and Selection of Specific Anti-Tau VHH After 3 immunizations, the sera of Inti (brain extract) and Rascar (tau-pS422) were collected and their binding to phospho-tau and non phosphorylated tau was analyzed by ELISA (FIG. 1). The sera of Inti and Rascar recognized both phosphorylated tau and non phosphorylated tau, although the immune response of Inti appeared to be better than that of Rascar. However, the former did not distinguish significantly phospho-tau and non phospho-tau and the latter showed a higher immune response for phospho-tau.

In order to ensure that one or some of anti phospho-tau antibodies present in the sera could recognize tau lesions in fixed mouse tissues, IHC was performed on both frozen microtome floating sections and non-frozen vibratome floating sections from TauPS2APP mice (Grueninger F. et al., 2010, Neurobiol Dis., 37:294-306). The serum of Inti did not show any immune staining of tau lesions but otherwise the serum of Rascar demonstrated a specific tau staining of NFTs on both microtome and vibratome sections (data not shown).

Despite the absence of immunodetection for NFTs in IHC with Inti polyclonal serum, it can not be excluded the existence of phospho-tau specific antibodies in its blood plasma. Indeed, the lack of IHC signal could be due to the low frequency of anti phospho-tau antibodies, which could recognize the epitopes of phospho-tau present in NFTs of TauPS2APP mice. The two libraries obtained from these two animals were pooled for panning experiments.

Total RNA from peripheral blood lymphocytes was used as template for cDNA synthesis. Using this cDNA, the VHH encoding sequences were then amplified by PCR and cloned into vector pHEN1. Subsequent transformations yielded two libraries of about $3 \times 10^8$ clones each. Both libraries were pooled and VHHs displaying the best affinity were selected by phage display through 3 panning cycles with phosphorylated tau. 96 individual clones were tested by ELISA on phosphorylated tau and on tau proteins. Only one clone was found to bind specifically on phosphorylated tau (VHH Tau-A2).

This VHH was subcloned in vector pET23 or in vector pASK IBA2 to allow a high level of expression of VHH with, respectively, a His-tag or a Streptavidin-tag. Yields of <1 mg/l of bacterial culture were obtained. The single domain products were shown to be pure to homogeneity by SDS-PAGE and by RP-HPLC/MS (data not shown); its pI values was above 9.5. Dynamic light scattering experiments showed that Tau-A2 is monomeric (RH=4.5±0.3 nm) and is not aggregated after purification. Amino-acid sequence of VHH Tau-A2 is referred to as SEQ ID NO. 4.

2. Recognition of NFTs by VHH Tau-A2

Figure 2:
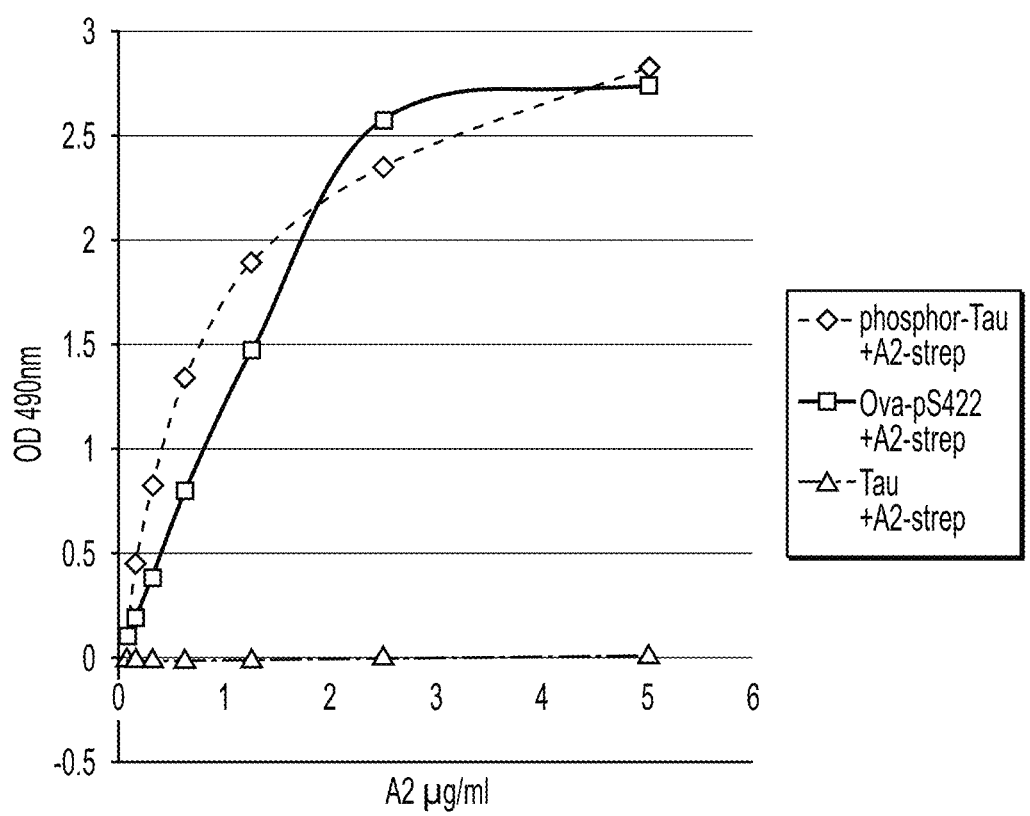
FIG. 2 shows the binding of purified VHH Tau-A2 to phospho-tau, tau (unphosphorylated) and Ova-pS422 peptide.

2.1 VHH Tau A2 Recognizes the Phosphorylated Serine 422 in the C-Ter Tau Peptide Several serine and threonine are phosphorylated on the pathogenic form of tau. To evaluate the role of phosphorylation in the epitope recognition, ELISA was performed on phosphorylated tau and single phospho-peptide derived from the C-terminus of a tau protein (sequence CSIDMVDS (PO$_3$H$_2$)PQLATLAD; SEQ ID NO. 6), coupled to ovalbumin (Ova) protein. Phosphorylated tau was the full-length tau protein phosphorylated at multiple sites including S422. VHH Tau-A2 binds both compounds suggesting that VHH Tau-A2 recognized an epitope including the phospho serine 422 (pS422) (FIG. 2).

2.2 Immunoreactivity of VHH Tau A2 for NFTs

The distribution of VHH-specific immunoreactivity was examined in human AD brains, in tissues from other tauopathies (fronto-temporal dementia [FTD], progressive supranuclear palsy [PSP] and Pick's disease [PD]) and in transgenic Tg4510 mice brains.

Figure 3A:
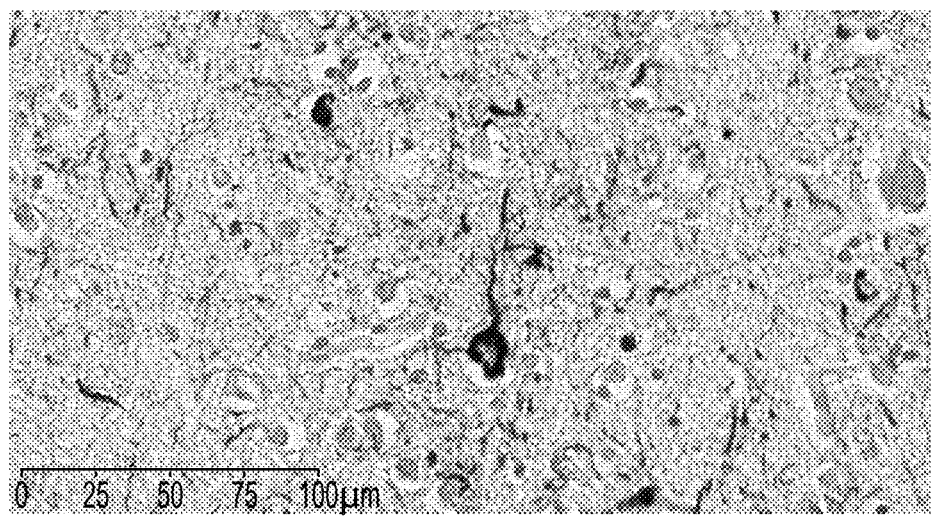
FIGS. 3A to 3B show the immunohistochemical staining of NFTs using the VHH Tau-A2 and mAb AT8 on human paraffin sections from cases with various tauopathies: AD (FIG. 3A), FTD (FIG. 3B), PSP (FIG. 3B) and PD (FIG. 3C).
Figure 3A:
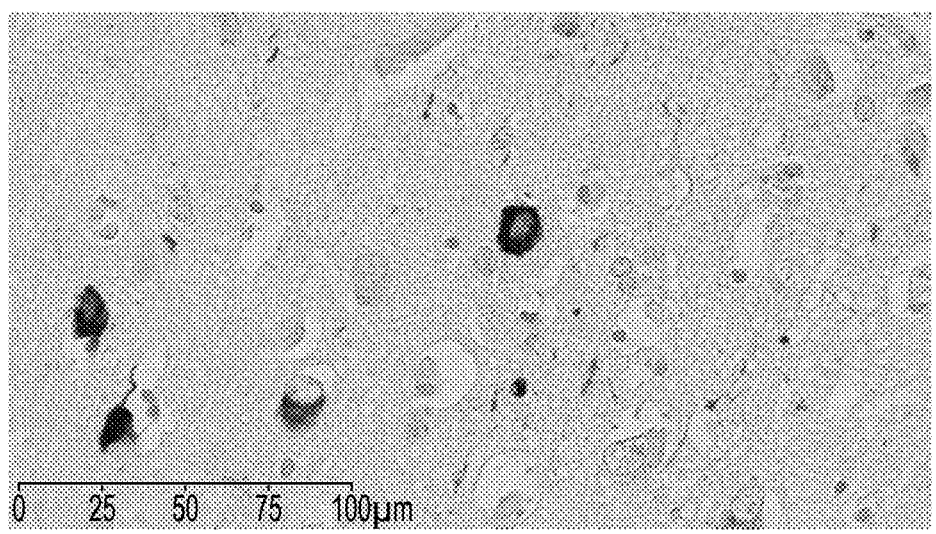
Figure 3B:
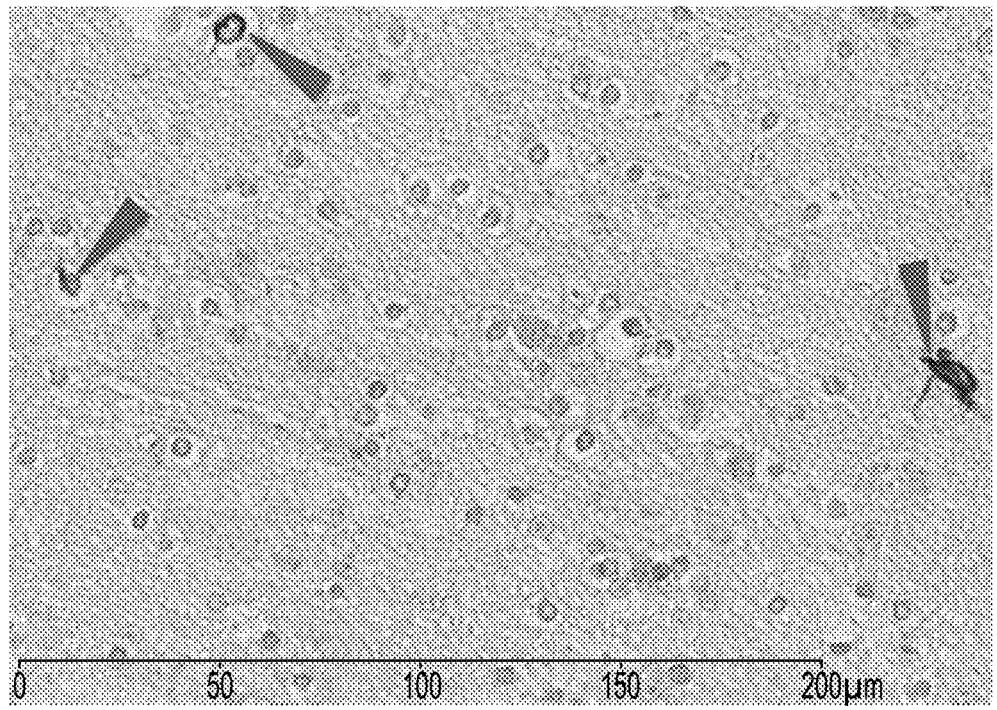
Figure 3B:
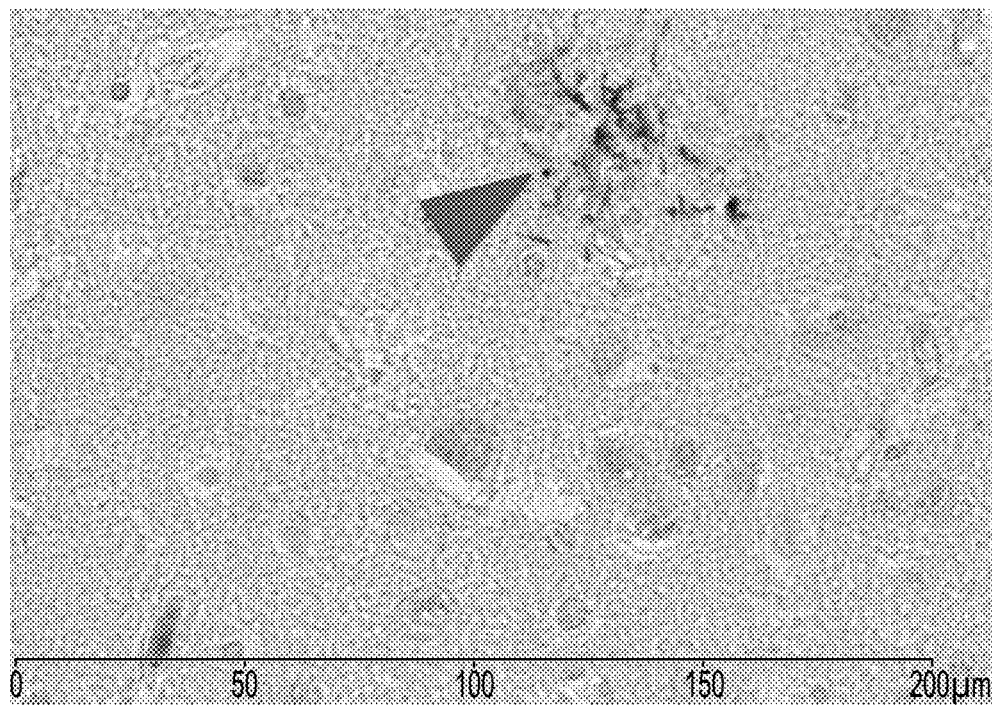
Figure 3C:
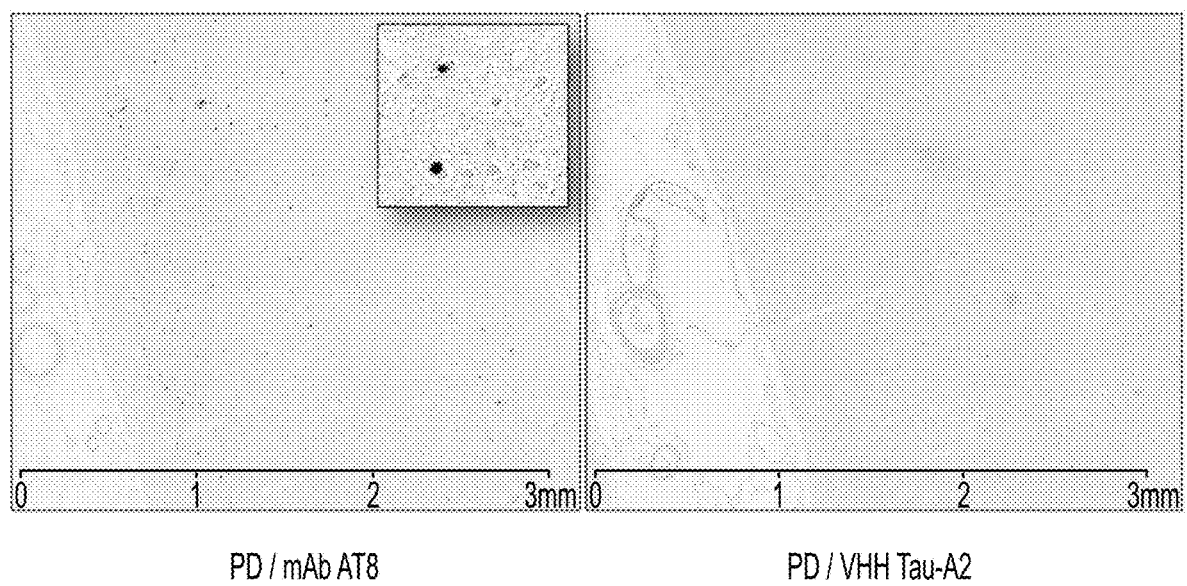

VHH Tau-A2 showed good ability to immunodetect NFTs in paraffin sections from AD patients (FIG. 3A). Also tau-positive glial inclusions were observed in the FTD case (oligodendroglial coiled bodies) and in the PSP case (astrocytic tufts) (FIG. 3B). Interestingly the typical cellular inclusions (Pick bodies) identified by the reference anti-tau AT8 mAb were negative for Tau-A2 (FIG. 3C) underlining some specificity of the VHH. As opposed to other tauopathies Pick bodies are only constituted of 3R tau proteins. Hence it can be hypothesized that Tau-A2 mainly recognizes tau with 4 repeats. No labeling was observed with tissues from wild type mice.

Figure 4:
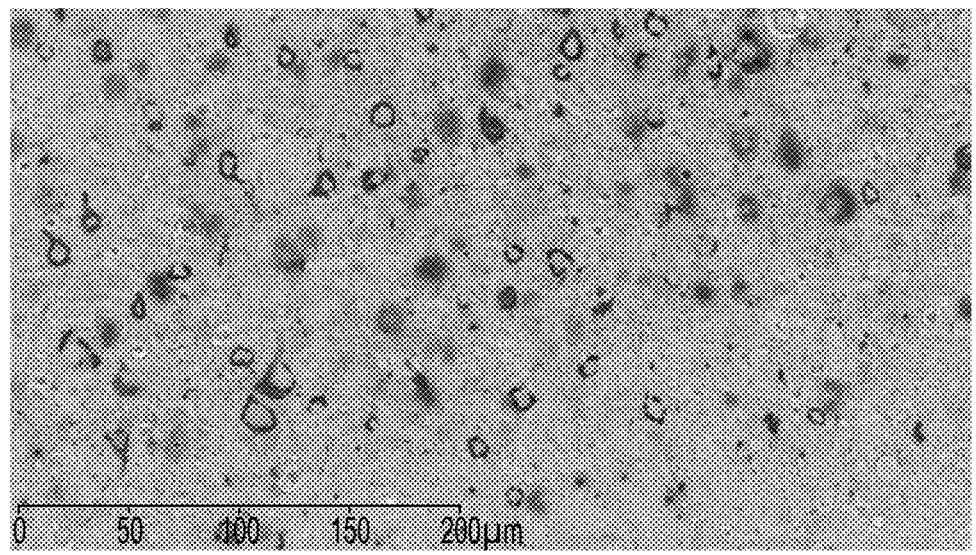
FIG. 4 shows the immunohistochemical staining of NFTs using the VHH Tau-A2 and mAb AT8 on Tg4510 mouse free-floating sections.
Figure 4:
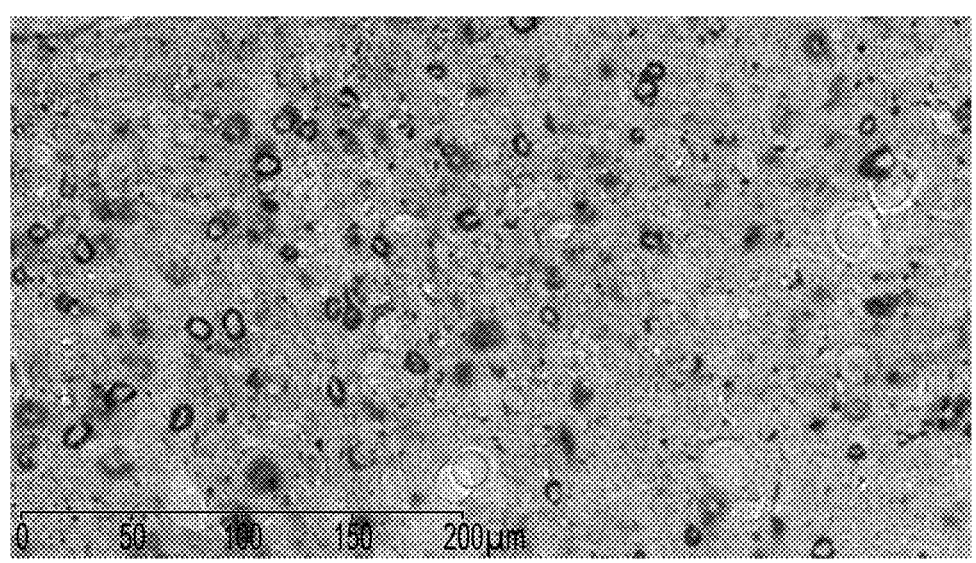

Paralleling result on paraffin-embedded tissues, it was showed that NFT immunodetection using VHH Tau-A2 can be readily obtained on mouse free-floating vibratome sections (FIG. 4).

Figure 5:
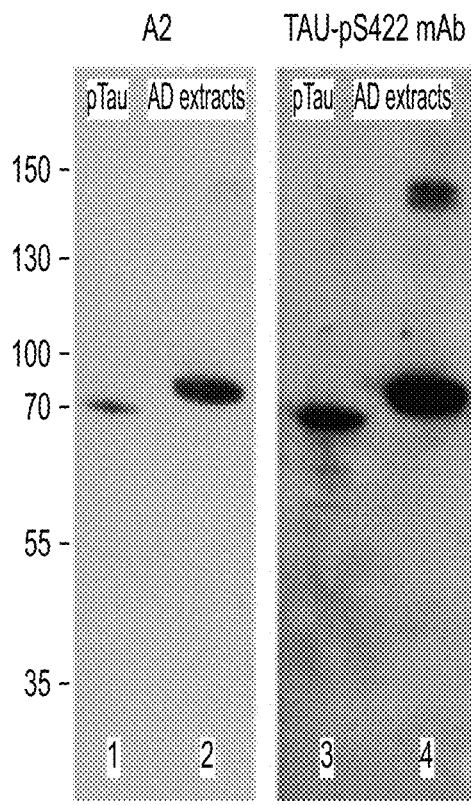
FIG. 5 shows a western blot on AD brain extracts and phospho-tau (p-tau) revealed by VHH Tau-A2 and Tau-pS422 mAb. Lane 1 and 3: p-tau+Tau-A2 and Tau-pS422 mAb, respectively. Lane 2 and 4: AD extracts+Tau-A2 and Tau-pS422 mAb, respectively.

To confirm the immunoreactivity of VHH Tau-A2 on brain tissues, western-blot immunoassays were performed on brain extracts obtained from AD patients. Tau-pS422 mAb (Grueninger et al. 2011 Mol Cell Biochem., 357, 199-207) was used as a reference antibody. Recombinant phospho-tau (p-tau) was loaded in parallel on SDS-PAGE gel. Phospho-tau protein was revealed by both VHH Tau-A2 and Tau-pS422 mAb. One main band, corresponding to phosphorylated tau between 70 and 100 kDa, was immunodetected with Tau-A2 and Tau-pS422 in AD extracts. With Tau-pS422 mAb, two additional bands with a molecular weight between 130 and 150 kDa were observed indicated the presence of aggregated tau-pS422 in AD brain, which was very slightly revealed by Tau-A2 (FIG. 5).

3. Cys-Engineered Tau-A2 and Antibody Coupling to Alexa Fluor® 488 Maleimide

Figure 7A:
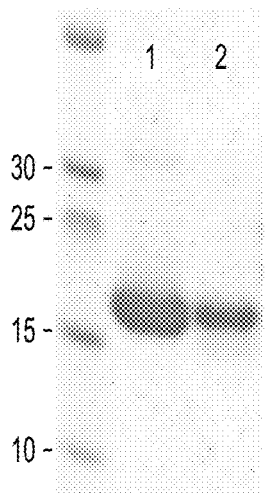
FIGS. 7A to 7F show the biochemical and histological characterization of Tau-A2 and its derivatives. A: Protein profile analysis of VHH Tau-A2-SH (lane 1) and Tau-A2-S-AF488 (lane 2) by instantBlue stained SDS-PAGE gel. B: Determination of pI of Tau-A2 derivatives by NEPHGE on 3-10 IEF gel. C: In vitro imaging of NFTs by Tau-A2-S-AF488 on Tg4510 paraffin sections. The presence of VHH was revealed by the addition of a rabbit polyclonal antibodies directed against VHH. D: Negative control: IHC on TauPS2APP VHH free paraffin section using rabbit anti-VHH Tau-A2 only. E: Direct fluorescent staining of NFTs by Tau-A2-S-AF488 in the cortex on Tg4510 free floating sections. F: Direct fluorescent staining of NFTs by Tau-A2-S-AF488 in the hippocampus on Tg4510 free floating sections.
Figure 7B:
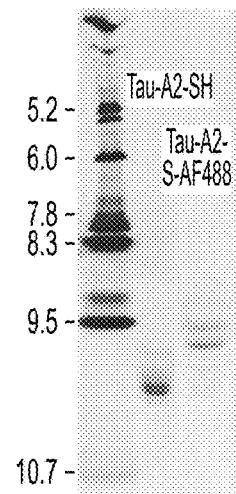

Cys-engineered Tau-A2 containing from the N to the C terminus a 6-Histidine tag, a thrombin cleavage site, VHH Tau-A2 sequence followed by a G3 S spacer and three extra amino acids CSA was cloned in vector pET23d to allow a high level of expression (referred to as Tau-A2-SH or A2-SH; SEQ ID NO. 14). Tau-A2-SH was conjugated to maleimido Alexa Fluor® 488 by thioaddition. The resulting product Tau-A2-S-AF488 was analyzed by SDS-PAGE, IEF/NEPGHE (FIGS. 7A and 7B) and RP-HPLC/MS. It was shown to be pure to homogeneity by SDS-PAGE and by RP-HPLC/MS. All analyses showed that Tau-A2-SH was totally converted into the well-defined conjugate, referred to as Tau-A2-S-AF488, with a single AF488 on the VHH Tau-A2. Tau-A2-SH possesses a pI around 10 (between 9.5 and 10.5) and this value slightly decreases after AF488 conjugation, still remaining>9.5 (see FIG. 7B). The hydrodynamic radius ($R_H$) of Tau-A2-SH and Tau-A2-S-AF488 was separately measured by DLS. The size distribution over time showed an average $R_H$ of 2.66±0.0788 nm for Tau-A2-SH and an average $R_H$ of 3.576±0.225 nm for Tau-A2-S-AF488, which suggested that both of them were in monomeric form in solution.

4. Detection of NFTs with VHH Tau-A2-S-AF488

4.1 In Vitro Labeling on Brain Slices of Tg4510 Mouse

Figure 7C:
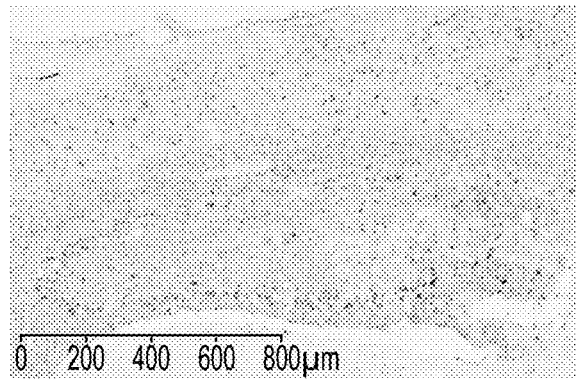
Figure 7D:
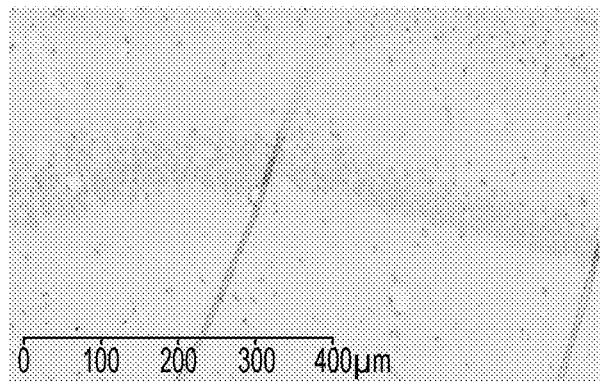
Figure 7E:
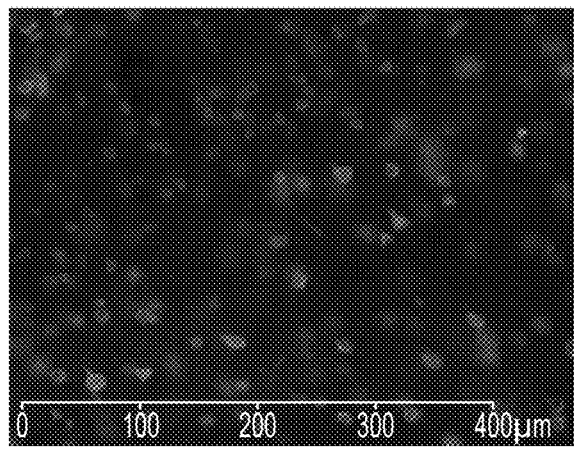
Figure 7F:
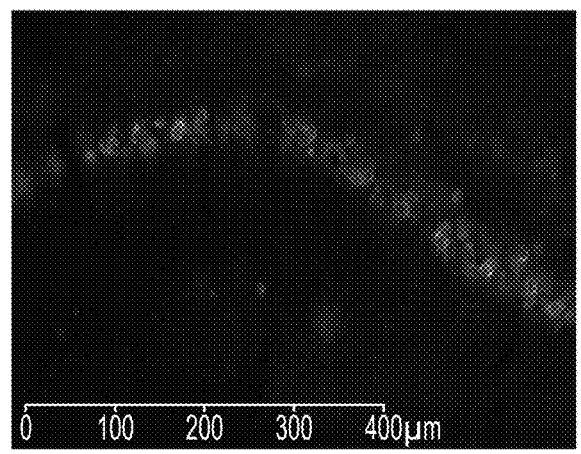

After direct incubation with mouse brain sections, Tau-A2-S-AF488 showed good ability to detect NFTs in Tg4510 mice by standard IHC (FIG. 7C-D), and direct fluorescent staining (FIG. 7E-F).

4.2 Two Photon Imaging After Intracerebral Injection

Figure 8:
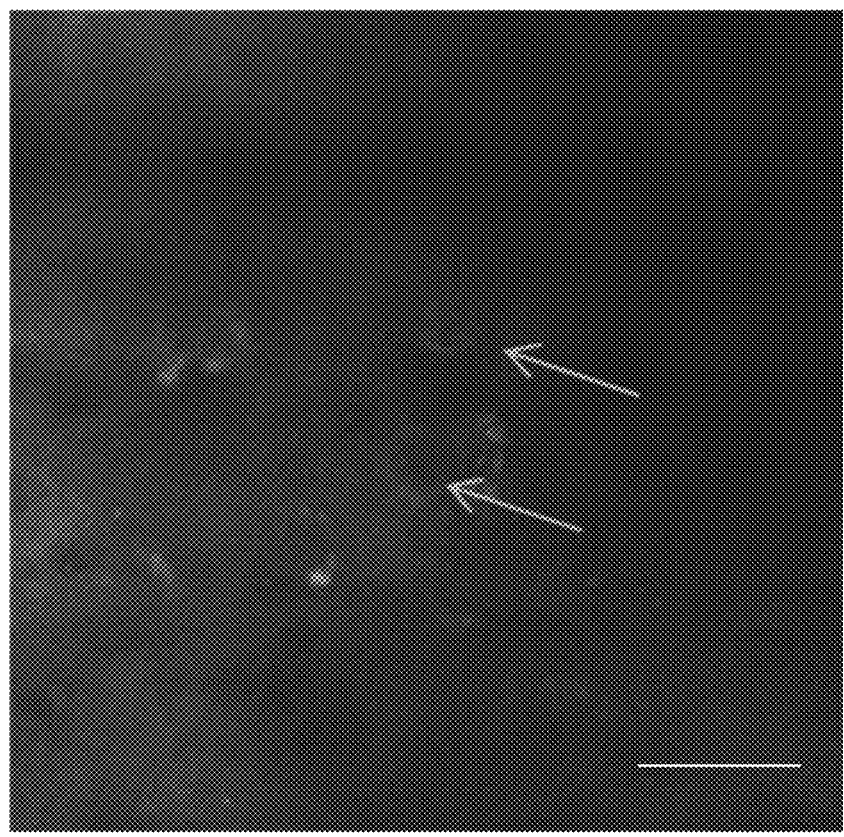
FIG. 8 shows the in vivo imaging of NFTs after cerebral injection of Tau-A2-S-AF488 in a 8-month-old Tg4510 mouse. Arrows indicate labeling of NFTs. Scale bar=50 µm.

In vivo two-photon imaging of Tau-A2-S-AF488 was performed after direct intracerebral injection of 1.2 µg (1.5 µL) in a Tg4510 mouse brain following a craniotomy and perforation of the dura mater. A large amount of CSF was observed and a high auto-fluorescence (even before the injection) was observed. Despite these limitations for appropriate bi-photon imaging, specific staining of NFTs was detected after topic cortical injection (FIG. 8).

4.3 Two-Photon Imaging After Intravenous Injection of VHH Tau-A2-S-AF488

Figure 9A:
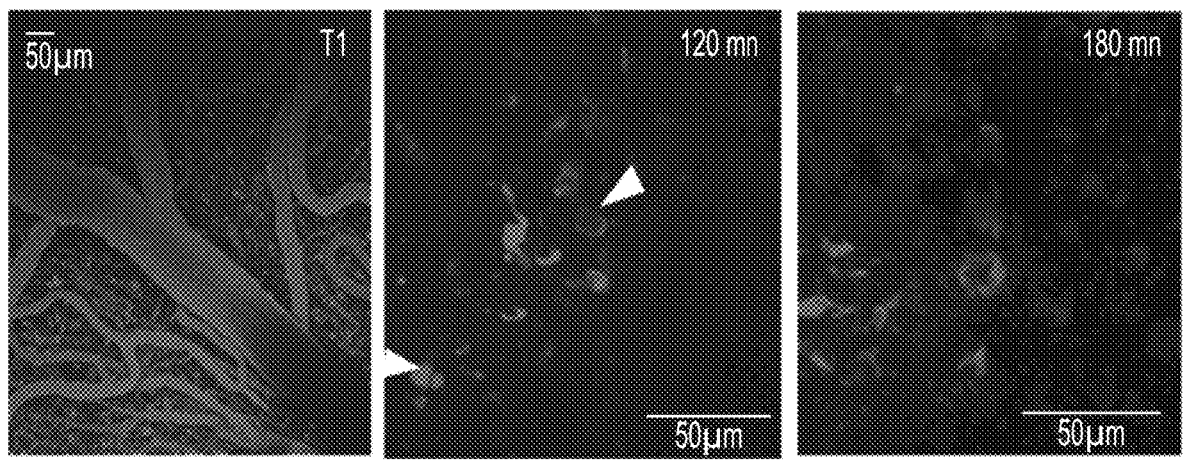
FIGS. 9A to 9B show the in vivo two-photon imaging of Tau-A2-S-AF488 diffusing from blood vessels and labeling NFTs. A: Maximum intensity projection of fluorescence in a cortical area of a Tg4510 mouse 1 min, 120 min, 180 min after intravenous injection of Tau-A2-S-AF488 at 10 mg/kg. Whereas only faint non-specific signal could be detected before iv injection, a strong staining of arborescent vessels was observed few second after iv injection (T1). Specific labeling of NFTs (white arrows) was observed after 120 min, with a maximum intensity after 180 min (3D reconstruction (MIP)). Experiments were performed on 2 mice. B: Four hours after IV injection of Tau-A2-S-AF488, the brain was harvested and IHC was performed on 5 µm-paraffin sections. Rabbit polyclonal anti-VHH antibodies were used to reveal the presence and the labeling of NFTs by Tau-A2-S-AF488.

A 10 mg/kg dose of Tau-A2-S-AF488 was injected in the tail vein (270 µg, 150 µL) of two Tg4510 mice. BBB integrity of these mice was previously checked by MRI and absence of signal modification in the mice suggested no disruption of BBB (data not shown). The conjugate extravasation and staining in the brain was recorded for 4 hours post injection using two-photon microscopy on brain window (z=from the surface up to 360 µm deep). FIG. 9A displayed in vivo imaging (Maximum Intensity Projection—MIP) of Tau-A2-S-AF488 over time up to 180 min in the same region. Few seconds after iv injection, strong staining of arborescent vessels was observed and declined dramatically 20 min later with only few capillary vessels remaining stained. This suggested a short half-life of conjugated VHH in the circulation (10-20 min). 120 min after iv injection, NFTs began to be visualized. The absence of signal in the red channel demonstrated that the fluorescent signal was specific (data not shown) and not due to general autofluorescence. VHH Tau-A2-S-AF488 extravasation and staining in the brain was registered for 3 hours post injection using two-photon microscopy on brain window (from the immediate cortical surface up to 350 µm deep). In addition to strong auto-fluorescence background and large amount of CSF (see above), the Tg4510 mice exhibited marked cerebral atrophy. A few seconds after iv injection, strong staining of densely-packed vessels was observed. Specific tau staining of NFTs was observed 2 h after injection despite remaining autofluorescence signal. A persistent and specific labeling of NFTs was observed even 3 hours after injection (FIG. 9A), suggesting a brain half-life of Tau-A2-S-AF488 extending over several hours.

Figure 9B:
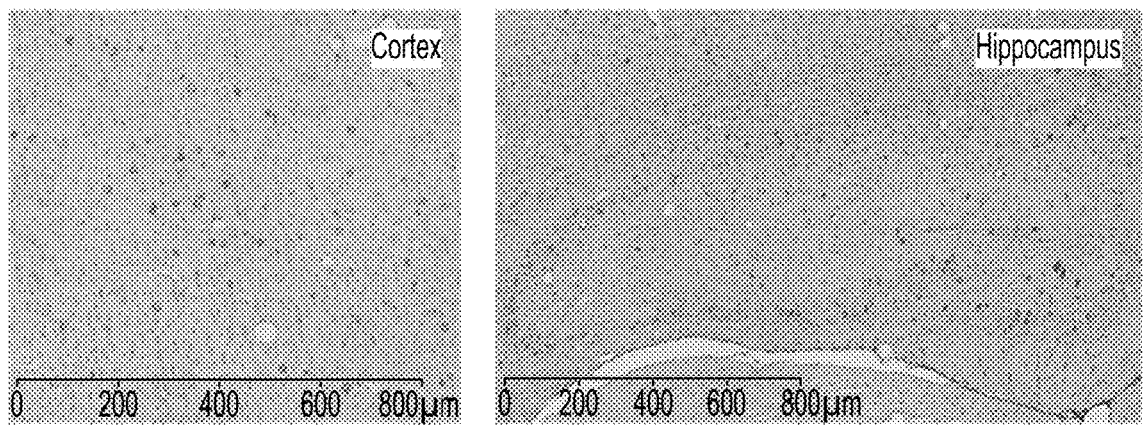
Figure 9B:
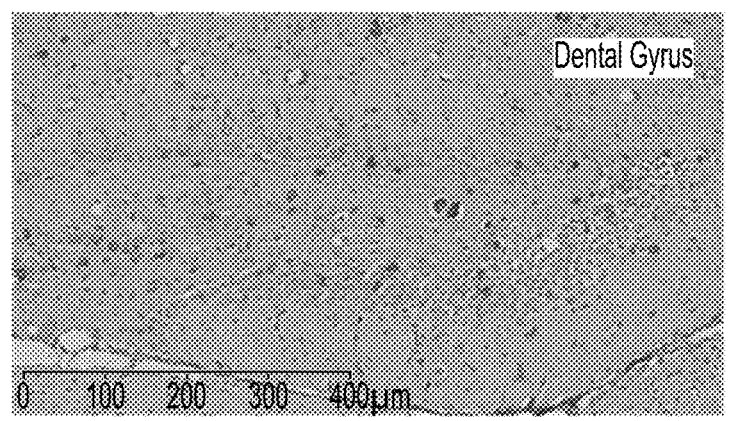

Four hours after the intravenous injection of Tau-A2-S-AF488, the brain was harvested and 5 µm-thick paraffin sections were prepared. IHC was then performed with rabbit polyclonal anti-VHH antibodies to confirm the diffusion and labeling of NFTs by Tau-A2-S-AF488 (FIG. 9B).

6. Control Experiments

Evaluation in NFTs-Free Mouse

Tau-A2-S-AF488 was intravenously injected in a wild type, NFT-free, C57BL/6 mouse. No specific in vivo staining in the brain parenchyma was observed using two-photon microscopy assay (data not shown).

Comparison with Conventional IgG Antibody

Injection of AF488-conjugated anti-Tau mAb (Grueninger et al. 2010 *Neurobiol. Dis.*, 37, 294-306) iv in a Tg4510 mouse did not allow detection of NFTs indicating no significant extravasation of this standard anti-Tau-pS422 immunoglobulin.

7. Conclusion

Using two-photon microscopy after iv injection, VHH Tau-A2-S-AF488 showed its ability to cross the BBB and to penetrate into neurons after crossing a second (plasma membrane) barrier to reach its cytoplasmic target. Long-term detection (3 h) of NFTs labeling suggested also a long half-life of this VHH in the brain.

8. Antibody Coupling to MRI Contrast Agent

VHH Tau-A2-SH was labeled with gadolinium (MRI contrast agent) using 1,4,7,10 tetraazacyclododecane-1,4,7,10-tetraacetic acid (DOTA) as the chelating agent. A site specific coupling strategy was used which involves the thioaddition of Tau-A2-SH to the synthetic maleimido-(DOTA/Gd)3 compound. Tau-A2-SH was totally converted into the well-defined conjugate Tau-A2-S-(DOTA/Gd)$_3$, as shown by RP-HPLC/MS, with 65% yield. The pI of Tau-A2-S-(DOTA/Gd)$_3$ was slightly reduced compared to the one of the unlabeled Tau-A2-SH (data not shown).

EXAMPLE II

Synthesis of a Variant of Tau-A2-SH: Tau-A2Var-SH

VHH Tau-A2 specifically detected phosphorylated Tau but its production level is rather low, in average 150 µg/L, and it tends to aggregate. It was therefore needed to provide a variant of VHH Tau-A2 with improved properties.

Figure 10:
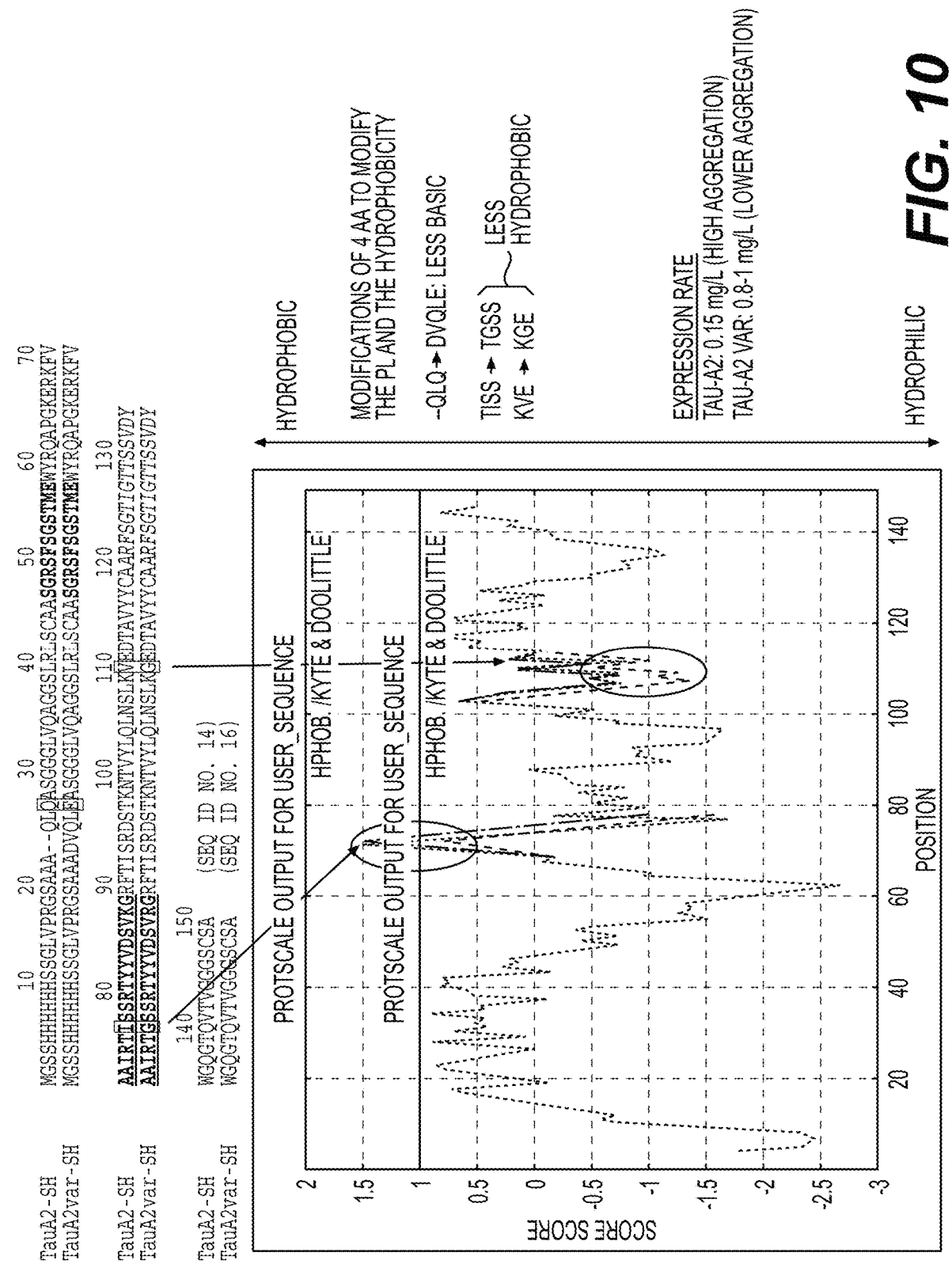
FIG. 10 shows the optimization of the amino acid sequence of Tau-A2-SH for expression. Tau-A2-SH of SEQ ID NO. 14. Tau-A2var-SH of SEQ ID NO. 17.

Two hydrophobic amino acids located in 2 hydrophobic areas of VHH Tau-A2-SH of SEQ ID NO. 14 were mutated: isoleucine at position 76 replaced by a glycine (I76G) and valine at position 110 by a glycine (V110G) (FIG. 10). These mutations increased the hydrophilicity of the VHH with an increase of the GRAVY index from −0.280 for Tau-A2-SH to −0.365 for the variant (GRAVY or Grand average of hydropathicity index indicates the solubility of the proteins: positive GRAVY (hydrophobic), negative GRAVY (hydrophilic)). Glutamine at position 26 was also mutated by a glutamic acid (Q26E) and an aspartic acid (D) and anvaline (V) were added between position 22 and 23 to slightly decrease the pI (less basic) (FIG. 10). Three of these mutated amino acids (D23, E26, and G110) are located outside the CDRs. This mutant is referred to as Tau-A2var-SH (SEQ ID NO. 17).

Figure 11D:
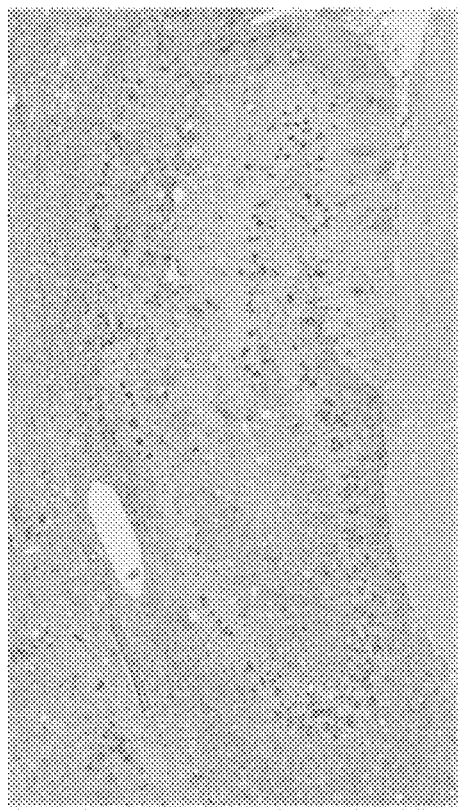
Figure 11D:
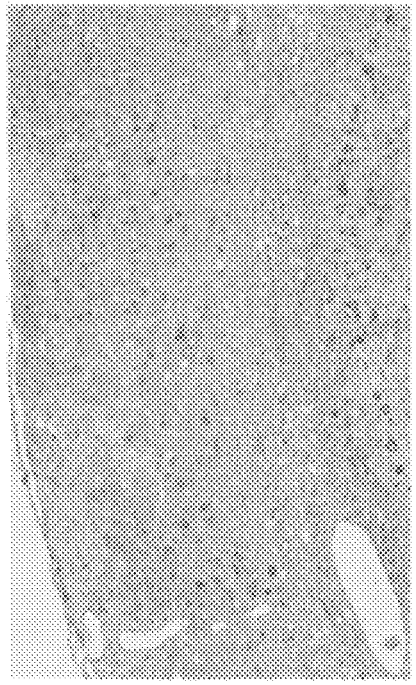
Figure 11D:
Figure 11D:
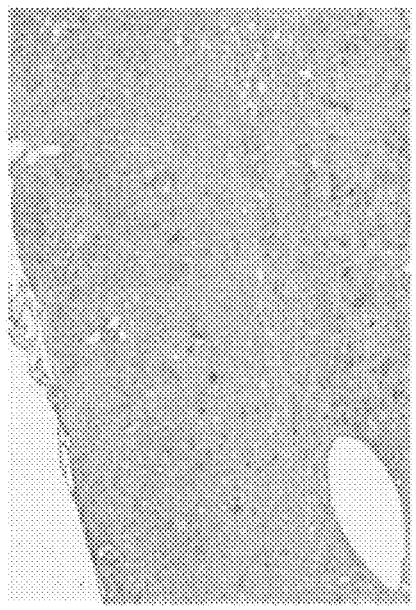

VHH Tau-A2var-SH (SEQ ID NO. 17) was cloned in pET23d vector and expressed in *E. coli*. It was purified on a Ni-NTA resin by elution in imidazole. Analyses of Tau-A2-SH in comparison with Tau-A2var-SH were performed by several methods:

SDS-PAGE showed only one band at an apparent molecular weight around 15-16 KDa (FIG. 11A). A better production of Tau-A2var-SH was observed with an expression rate estimated to 0.8-1 mg/L, 5 times more than the parental counterpart. Moreover Tau-A2var-SH has a lower tendency to aggregate. The pI is 9.68 slightly less basic than Tau-A2-SH (FIG. 11B).

the ability of both VHHs to recognize phospho-Tau was evaluated by ELISA (FIG. 11C). Comparison of the binding curves of Tau-A2var-SH and Tau-A2-SH did not show any difference for their recognition of phospho-Tau (FIG. 11C).

to further assess the functional activity of Tau-A2var-SH, IHC was then carried out on tissue from mice model of NFTs (Tg4510 mice). After incubation of the brain slices with the different compounds and revelation by an anti-His secondary antibody, a detection of NFTs was observed with both compounds on mouse tissues (FIG. 11D). Immunostaining was even slightly enhanced using Tau-A2var as compared to Tau-A2.

The VHH Tau-A2var-SH was labeled using a similar procedure on the non-dialized protein solution, directly after the affinity column elution.

Figure 12:
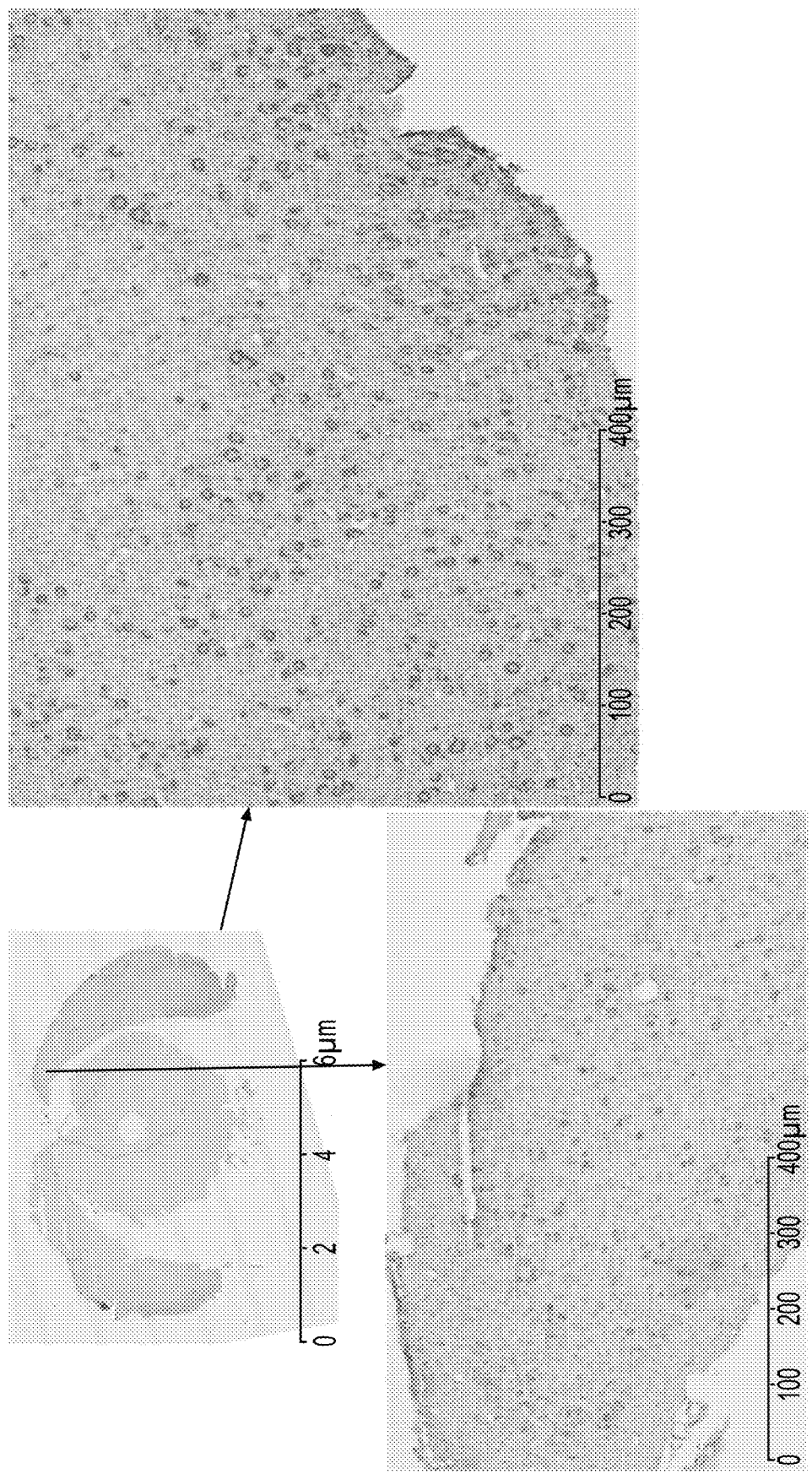
FIG. 12 shows the in vivo imaging of NFTs after intravenous injection of Tau-A2var-S-(DOTA/Gd)$_3$ in a 8-month-old Tg4510 mouse. Four hours after IV injection of Tau-A2var-S-(DOTA/Gd)$_3$, the brain was harvested and IHC was performed on 5 µm-paraffin sections. Rabbit polyclonal anti-VHH antibodies were used to reveal the presence and the labeling of NFTs by Tau-A2var-S-(DOTA/Gd)$_3$.

Then the ability of in vivo detection of NFTs with VHH Tau-A2var-S-(DOTA/Gd)$_3$ have been realized. A 10 mg/kg dose of Tau-A2var-S-(DOTA/Gd)$_3$ was injected in the tail vein (270 µg, 150 µL) of two Tg4510 mice. Four hours after the intravenous injection of Tau-A2var-S-(DOTA/Gd)$_3$, the brain was harvested and 5 µm-thick paraffin sections were prepared. IHC was then performed with rabbit polyclonal anti-VHH antibodies. NFTs were labeled in the cortex (FIG. 12). These data confirm the brain penetration, diffusion and labeling of NFTs by Tau-A2var-S-(DOTA/Gd)$_3$.

CONCLUSION

These results show that Tau-A2var behaves in a similar way as Tau-A2 for the recognition of phospho tau and NFTs. Using IHC studies after iv injection, VHH Tau-A2var-S-(DOTA/Gd)$_3$ showed its ability to cross the BBB and to penetrate into neurons after crossing a second (plasma membrane) barrier to reach its cytoplasmic target.

The invention claimed is:

1. An in vitro or ex vivo method, comprising:
   a) contacting in vitro a biological sample from a subject with a diagnostic agent comprising an isolated variant of the variable domain of a camelid heavy-chain antibody (VHH) of SEQ ID NO. 5 linked, directly or indirectly, covalently or non-covalently to a substance of interest, wherein said VHH variant is directed against the phosphorylated serine 422 of a phosphorylated tau protein, and wherein the amino acid sequence of said variant has at least 95% identity with the amino acid sequence SEQ ID NO: 5, and
   b) determining the presence or the absence of phosphorylated-tau protein in said biological sample.

2. The method of claim 1, wherein the amino acid sequence of said variant comprises, from the N-terminus to the C-terminus, the amino acid sequence SEQ ID NO. 1, the amino acid sequence SEQ ID NO. 2 and the amino acid sequence SEQ ID NO. 3.

3. The method of claim 1, wherein said variant has the amino acid sequence SEQ ID NO. 5 having the following mutations:
   A) the Glutamine residue (Gln, Q) at position 3 of the amino acid sequence SEQ ID NO. 5 is substituted with an amino acid residue selected from the group consisting of Aspartic acid (Asp, D) and Glutamic acid (Glu, E),
   B) the Isoleucine residue (Ile, I) at position 52 of the amino acid sequence SEQ ID NO. 5 is substituted with an amino acid residue selected from the group consisting of Alanine (Ala, A), Glycine (Gly, G), and
   C) the Valine residue (Val, V) at position 86 of the amino acid sequence SEQ ID NO. 5 is substituted with an amino acid residue selected from the group consisting of Alanine (Ala, A), Serine (Ser, S), Threonine (Thr, T), Asparagine (Asn, N), Glutamine (Gin, Q), Aspartic acid (Asp, D), Glutamic acid (Glu, E), Lysine (Lys, K), Arginine (Arg, R) and Glycine (Gly, G).

4. The method of claim 1, wherein said variant consists of the amino acid sequence of SEQ ID NO. 15 or of the amino acid sequence of SEQ ID NO. 16.

5. The method of claim 1, wherein the subject has a disorder selected from tauopathies, Alzheimer's disease (AD), Pick disease (PD), fronto-temporal dementia (FTD), corticobasal degeneration (CBD) and progressive supranuclear palsy (PSP).

6. The method of claim 1, wherein the presence of said phosphorylated-tau protein indicates that said subject has a disorder selected from tauopathies, Alzheimer's disease (AD), Pick disease (PD), fronto-temporal dementia (FTD), corticobasal degeneration (CBD) and progressive supranuclear palsy (PSP).

7. The method of claim 1, wherein the substance of interest is selected from the group consisting of an enzyme, a fluorophore, a Nuclear Magnetic Resonance (NMR) or Magnetic Resonance Imaging (MRI) contrast agent, a radioisotope, and a nanoparticle.

8. An in vitro or ex vivo method, comprising:
   a) providing a biological sample from a subject having a disorder selected from tauopathies, Alzheimer's disease (AD), Pick disease (PD), fronto-temporal dementia (FTD), corticobasal degeneration (CBD) and progressive supranuclear palsy (PSP),
   b) contacting in vitro the biological sample with a diagnostic agent comprising an isolated variant of the variable domain of a camelid heavy-chain antibody (VHH) of SEQ ID NO. 5 linked, directly or indirectly, covalently or non-covalently to a substance of interest, wherein said VHH variant is directed against the phosphorylated serine 422 of a phosphorylated tau protein, and wherein the amino acid sequence of said variant has at least 95% identity with the amino acid sequence SEQ ID NO: 5, and
   c) measuring the amount of phosphorylated-tau protein in said biological sample, and
   d) comparing the amount measured in step c) with an amount of phosphorylated-tau protein previously measured in said subject.

9. The method of claim 8, wherein the amino acid sequence of said variant comprises, from the N-terminus to the C-terminus, the amino acid sequence SEQ ID NO. 1, the amino acid sequence SEQ ID NO. 2 and the amino acid sequence SEQ ID NO. 3.

10. The method of claim 8, wherein said variant has the amino acid sequence SEQ ID NO. 5 having the following mutations:
    A) the Glutamine residue (Gln, Q) at position 3 of the amino acid sequence SEQ ID NO. 5 is substituted with an amino acid residue selected from the group consisting of Aspartic acid (Asp, D) and Glutamic acid (Glu, E),
    B) the Isoleucine residue (Ile, I) at position 52 of the amino acid sequence SEQ ID NO. 5 is substituted with an amino acid residue selected from the group consisting of Alanine (Ala, A), Glycine (Gly, G), and
    C) the Valine residue (Val, V) at position 86 of the amino acid sequence SEQ ID NO. 5 is substituted with an amino acid residue selected from the group consisting of Alanine (Ala, A), Serine (Ser, S), Threonine (Thr, T), Asparagine (Asn, N), Glutamine (Gin, Q), Aspartic acid (Asp, D), Glutamic acid (Glu, E), Lysine (Lys, K), Arginine (Arg, R) and Glycine (Gly, G).

11. The method of claim 8, wherein said variant consists of the amino acid sequence of SEQ ID NO. 15 or of the amino acid sequence of SEQ ID NO. 16.

12. The method of claim 8, wherein a significant increase in the amount of phosphorylated-tau protein is measured in step c) compared to the amount in a previous sample, and wherein the subject has progression of said disorder.

13. The method of claim 8, wherein a significant decrease in the amount of phosphorylated-tau protein is measured in step c) compared to the amount in a previous sample, and wherein the subject has regression of said disorder.

14. The method of claim 8, wherein the substance of interest is selected from the group consisting of an enzyme, a fluorophore, a Nuclear Magnetic Resonance (NMR) or Magnetic Resonance Imaging (MRI) contrast agent, a radioisotope, and a nanoparticle.

15. A method for in vivo imaging neurofibrillary tangles, neuropil threads or dystrophic neurites in a subject, comprising:
   a) administering to a subject a detectable quantity of a diagnostic agent comprising an isolated variant of the variable domain of a camelid heavy-chain antibody (VHH) of SEQ ID NO. 5 linked, directly or indirectly, covalently or non-covalently to a substance of interest, wherein said VHH variant is directed against the phosphorylated serine 422 of a phosphorylated tau protein, and wherein the amino acid sequence of said variant has at least 95% identity with the amino acid sequence SEQ ID NO: 5, and b) detecting the diagnostic agent in said subject by an imaging method.

16. The method of claim 15, wherein the amino acid sequence of said variant comprises, from the N-terminus to the C-terminus, the amino acid sequence SEQ ID NO. 1, the amino acid sequence SEQ ID NO. 2 and the amino acid sequence SEQ ID NO. 3.

17. The method of claim 15, wherein said variant has the amino acid sequence SEQ ID NO. 5 having the following mutations:
   A) the Glutamine residue (Gln, Q) at position 3 of the amino acid sequence SEQ ID NO. 5 is substituted with an amino acid residue selected from the group consisting of Aspartic acid (Asp, D) and Glutamic acid (Glu, E),
   B) the Isoleucine residue (Ile, I) at position 52 of the amino acid sequence SEQ ID NO. 5 is substituted with an amino acid residue selected from the group consisting of Alanine (Ala, A), Glycine (Gly, G), and
   C) the Valine residue (Val, V) at position 86 of the amino acid sequence SEQ ID NO. 5 is substituted with an amino acid residue selected from the group consisting of Alanine (Ala, A), Serine (Ser, S), Threonine (Thr, T), Asparagine (Asn, N), Glutamine (Gln, Q), Aspartic acid (Asp, D), Glutamic acid (Glu, E), Lysine (Lys, K), Arginine (Arg, R) and Glycine (Gly, G).

18. The method of claim 15, wherein said variant consists of the amino acid sequence of SEQ ID NO. 15 or of the amino acid sequence of SEQ ID NO. 16.

19. The method of claim 15, wherein the substance of interest is selected from the group consisting of an enzyme, a fluorophore, a Nuclear Magnetic Resonance (NMR) or Magnetic Resonance Imaging (MRI) contrast agent, a radioisotope, and a nanoparticle.

20. The method of claim 15, wherein the subject has a disorder selected from tauopathies, Alzheimer's disease (AD), Pick disease (PD), fronto-temporal dementia (FTD), corticobasal degeneration (CBD) and progressive supranuclear palsy (PSP).

\* \* \* \* \*